(12) United States Patent
Van Wyk et al.

(10) Patent No.: US 9,888,954 B2
(45) Date of Patent: Feb. 13, 2018

(54) PLASMA RESECTION ELECTRODE

(71) Applicants: Cook Medical Technologies LLC, Bloomington, IN (US); Electromedical Associates, LLC, Bethesda, MD (US)

(72) Inventors: Robert A. Van Wyk, St. Pete Beach, FL (US); Yuval Carmel, Bethesda, MD (US); Anatoly Shkvarunets, Rockville, MD (US); Shay Lavelle, Annacotty (IE); Therese Fitzgibbon, Newcastle West (IE); Kenneth C. Kennedy, II, Clemmons, NC (US)

(73) Assignees: Cook Medical Technologies LLC, Bloomington, IN (US); Electromedical Associates, LLC, Bethesda, MD (US)

( * ) Notice: Subject to any disclaimer, the term of this patent is extended or adjusted under 35 U.S.C. 154(b) by 678 days.

(21) Appl. No.: 13/963,437

(22) Filed: Aug. 9, 2013

(65) Prior Publication Data
US 2014/0088592 A1     Mar. 27, 2014

Related U.S. Application Data

(60) Provisional application No. 61/681,855, filed on Aug. 10, 2012.

(51) Int. Cl.
*A61B 18/14*     (2006.01)
*A61B 18/04*     (2006.01)
(Continued)

(52) U.S. Cl.
CPC .......... *A61B 18/042* (2013.01); *A61B 18/149* (2013.01); *A61B 2018/00101* (2013.01); *A61B 2018/122* (2013.01); *A61B 2018/1213* (2013.01)

(58) Field of Classification Search
CPC ................ A61B 18/042; A61B 18/149; A61B 2018/00101; A61B 2018/1213;
(Continued)

(56) References Cited

U.S. PATENT DOCUMENTS

| 2,448,741 A | 9/1948 | Scott et al. |
| 3,838,242 A | 9/1974 | Goucher |

(Continued)

FOREIGN PATENT DOCUMENTS

| CA | 1219642 | 3/1987 |
| EP | 1095627 A1 | 5/2001 |

(Continued)

OTHER PUBLICATIONS www.WiseTool.com, Coefficient of Thermal Expansion, printed Apr. 11, 2016, 2 pages.

*Primary Examiner* — Michael Peffley
*Assistant Examiner* — Khadijeh Vahdat
(74) *Attorney, Agent, or Firm* — Woodard, Emhardt, Moriarty, McNett & Henry LLP

(57) ABSTRACT

Disclosed herein are embodiments of an electrosurgical device that include one or more floating electrodes and are specifically adapted to remove, resect, ablate, vaporize, denaturize, coagulate and form lesions in soft tissues, preferably in combination with a resectoscope, particularly in the context of urological, gynecological, laparoscopic, arthroscopic, and ENT procedures. Specific adaptations for urological and gynecological applications, for example BPH treatment, are also described.

20 Claims, 26 Drawing Sheets

(51) Int. Cl.
*A61B 18/00* (2006.01)
*A61B 18/12* (2006.01)

(58) Field of Classification Search
CPC ... A61B 2018/122; A61B 18/04; A61B 18/08; A61B 18/082; A61B 18/10; A61B 18/12; A61B 18/1266; A61B 18/14; A61B 18/1442; A61B 18/1445; A61B 18/1448
USPC .......................................... 606/33–40, 41–50
See application file for complete search history.

(56) References Cited

U.S. PATENT DOCUMENTS

| | | | |
|---|---|---|---|
| 3,856,015 A | 12/1974 | Iglesias | |
| 3,901,242 A | 8/1975 | Storz | |
| 3,905,373 A | 9/1975 | Gonser | |
| 3,988,621 A | 10/1976 | Nakayama et al. | |
| 4,240,141 A | 12/1980 | Vasiliev et al. | |
| 4,282,763 A | 8/1981 | Griebeler | |
| 4,303,073 A | 12/1981 | Archibald | |
| 4,387,714 A | 6/1983 | Geddes et al. | |
| 4,583,529 A | 4/1986 | Briggs | |
| 4,674,498 A | 6/1987 | Stasz | |
| 4,674,499 A | 6/1987 | Pao | |
| 4,682,596 A | 7/1987 | Bales | |
| 4,692,139 A | 9/1987 | Stiles | |
| 4,726,370 A | 2/1988 | Karasawa | |
| 4,770,173 A | 9/1988 | Feucht et al. | |
| 4,832,048 A | 5/1989 | Cohen | |
| 4,844,099 A | 7/1989 | Skalsky et al. | |
| 4,901,719 A | 2/1990 | Trenconsky et al. | |
| 4,917,082 A | 4/1990 | Grossi et al. | |
| 4,936,281 A | 6/1990 | Stasz | |
| 5,000,573 A | 3/1991 | Hagen et al. | |
| 5,013,312 A | 5/1991 | Parins et al. | |
| 5,080,660 A | 1/1992 | Buelna | |
| 5,114,424 A | 5/1992 | Hagen et al. | |
| 5,190,517 A | 3/1993 | Zieve et al. | |
| 5,195,959 A | 3/1993 | Smith | |
| 5,261,905 A | 11/1993 | Doresey, III | |
| 5,277,696 A | 1/1994 | Hagen | |
| 5,282,799 A | 2/1994 | Rydell | |
| 5,300,068 A | 4/1994 | Rosar et al. | |
| 5,314,459 A | 5/1994 | Swanson et al. | |
| 5,320,635 A | 6/1994 | Smith | |
| 5,334,183 A | 8/1994 | Wuchinich | |
| 5,342,381 A | 8/1994 | Tidemand | |
| 5,465,171 A | 11/1995 | Weber et al. | |
| 5,527,331 A | 6/1996 | Kresch et al. | |
| 5,554,112 A | 9/1996 | Walbrink et al. | |
| 5,573,532 A | 11/1996 | Chang et al. | |
| 5,582,610 A | 12/1996 | Grossi et al. | |
| 5,598,966 A | 2/1997 | Romano et al. | |
| 5,647,840 A | 7/1997 | D'Amelio et al. | |
| 5,681,282 A | 10/1997 | Eggers et al. | |
| 5,688,269 A | 11/1997 | Newton et al. | |
| 5,697,536 A | 12/1997 | Eggers et al. | |
| 5,709,698 A | 1/1998 | Adams et al. | |
| 5,782,289 A | 7/1998 | Mastrorio et al. | |
| 5,782,829 A | 7/1998 | Swiantek et al. | |
| 5,782,891 A | 7/1998 | Hassler et al. | |
| 5,830,214 A | 11/1998 | Flom et al. | |
| 5,836,942 A | 11/1998 | Netherly et al. | |
| 5,873,855 A | 2/1999 | Eggers et al. | |
| 5,981,095 A | 4/1999 | Eggers et al. | |
| 5,918,354 A | 7/1999 | Ikegami et al. | |
| 6,015,406 A | 1/2000 | Goble et al. | |
| 6,024,742 A | 2/2000 | Tu et al. | |
| 6,033,400 A * | 3/2000 | Grossi .................. | A61B 18/149 606/41 |
| 6,050,993 A | 4/2000 | Tu et al. | |
| 6,053,910 A | 4/2000 | Fleenor | |
| 6,053,923 A | 4/2000 | Veca et al. | |
| 6,066,134 A | 5/2000 | Eggers | |
| 6,102,046 A | 8/2000 | Weinstein et al. | |
| 6,113,597 A | 9/2000 | Eggers et al. | |
| 6,142,996 A | 11/2000 | Mirhashemi et al. | |
| 6,159,194 A | 12/2000 | Eggers et al. | |
| 6,159,209 A | 12/2000 | Hakky | |
| 6,165,206 A | 12/2000 | Tu et al. | |
| 6,168,594 B1 | 1/2001 | LaFontaine et al. | |
| 6,169,926 B1 | 1/2001 | Baker | |
| 6,181,760 B1 | 1/2001 | Jinkim | |
| 6,197,025 B1 | 3/2001 | Grossi et al. | |
| 6,214,003 B1 | 4/2001 | Morgan et al. | |
| 6,222,307 B1 | 4/2001 | Roy et al. | |
| 6,235,020 B1 | 5/2001 | Cheng et al. | |
| 6,235,024 B1 | 5/2001 | Tu et al. | |
| 6,277,114 B1 * | 8/2001 | Bullivant ............. | A61B 18/149 606/41 |
| 6,296,638 B1 | 10/2001 | Davison et al. | |
| 6,312,405 B1 | 11/2001 | Eggers et al. | |
| 6,335,856 B1 | 1/2002 | Takeuchi et al. | |
| 6,371,956 B1 | 4/2002 | Wilson et al. | |
| 6,379,350 B1 | 4/2002 | Sharkey et al. | |
| 6,379,351 B1 | 4/2002 | Thapliyal et al. | |
| 6,391,025 B1 | 5/2002 | Weinstein et al. | |
| 6,419,684 B1 | 7/2002 | Heisler et al. | |
| 6,468,274 B1 | 10/2002 | Alleyne et al. | |
| 6,497,704 B2 | 12/2002 | Ein-Gal | |
| 6,514,248 B1 | 2/2003 | Eggers et al. | |
| 6,558,382 B2 | 5/2003 | Jahns et al. | |
| 6,565,560 B1 | 5/2003 | Goble et al. | |
| 6,565,561 B1 | 5/2003 | Goble et al. | |
| 6,575,968 B1 | 6/2003 | Eggers et al. | |
| 6,582,423 B1 | 6/2003 | Thapliyal et al. | |
| 6,589,237 B2 | 7/2003 | Woloszko | |
| 6,702,831 B2 | 3/2004 | Lee et al. | |
| 6,730,081 B1 * | 5/2004 | Desai ............... | A61B 17/00234 604/8 |
| 6,767,347 B2 | 7/2004 | Sharkey et al. | |
| 6,770,070 B1 | 8/2004 | Balbierz | |
| 6,796,982 B2 | 9/2004 | Carmel et al. | |
| 6,837,884 B2 | 1/2005 | Woloszko | |
| 6,840,937 B2 | 1/2005 | Van Wyk | |
| 6,899,712 B2 | 5/2005 | Moutafis et al. | |
| 6,920,883 B2 | 7/2005 | Bessette et al. | |
| 6,921,398 B2 | 7/2005 | Carmel et al. | |
| 6,921,399 B2 | 7/2005 | Carmel et al. | |
| 6,955,676 B2 | 10/2005 | Quick | |
| 6,971,391 B1 | 12/2005 | Wang et al. | |
| 7,066,936 B2 | 6/2006 | Ryan | |
| 7,118,574 B2 | 10/2006 | Patel et al. | |
| 7,150,748 B2 | 12/2006 | Ebbuttetal. | |
| 7,160,296 B2 | 1/2007 | Pearson et al. | |
| 7,166,193 B2 | 1/2007 | Carmel et al. | |
| 7,244,263 B2 | 7/2007 | Robison et al. | |
| 7,435,247 B2 | 10/2008 | Woloszko et al. | |
| 7,563,261 B2 | 7/2009 | Carmel et al. | |
| 7,566,333 B2 | 7/2009 | Van Wyk et al. | |
| 7,611,502 B2 | 11/2009 | Van Wyk | |
| 7,618,428 B2 | 11/2009 | O'Quinn et al. | |
| 7,771,419 B2 | 8/2010 | Carmel et al. | |
| 7,794,456 B2 | 9/2010 | Sharps et al. | |
| 7,837,683 B2 | 11/2010 | Carmel et al. | |
| 8,055,336 B1 | 11/2011 | Schulman et al. | |
| 8,192,432 B2 | 6/2012 | McGaffigan | |
| 8,308,724 B2 | 11/2012 | Carmel et al. | |
| 9,168,084 B2 | 10/2015 | Carmel et al. | |
| 2001/0001314 A1 | 5/2001 | Davison et al. | |
| 2002/0038122 A1 | 3/2002 | Peters | |
| 2002/0052600 A1 | 5/2002 | Davison et al. | |
| 2002/0072745 A1 | 6/2002 | Truckai et al. | |
| 2002/0120261 A1 | 8/2002 | Morris et al. | |
| 2002/0133148 A1 | 9/2002 | Daniel et al. | |
| 2002/0133149 A1 | 9/2002 | Bessette | |
| 2002/0146090 A1 | 10/2002 | Chornenky et al. | |
| 2003/0083655 A1 | 5/2003 | Van Wyk | |
| 2003/0088243 A1 | 5/2003 | Carmel et al. | |
| 2003/0120269 A1 | 6/2003 | Bessette et al. | |
| 2003/0146206 A1 | 8/2003 | Tanaka et al. | |
| 2003/0211407 A1 | 11/2003 | Watanabe et al. | |
| 2004/0006336 A1 | 1/2004 | Swanson | |
| 2004/0006339 A1 | 1/2004 | Underwood et al. | |

(56) References Cited

U.S. PATENT DOCUMENTS

| | | |
|---|---|---|
| 2004/0027034 A1 | 2/2004 | Kawaguchi et al. |
| 2004/0030330 A1 | 2/2004 | Brassell et al. |
| 2004/0046557 A1 | 3/2004 | Karmarkar et al. |
| 2004/0049183 A1 | 3/2004 | Ellman et al. |
| 2004/0088032 A1 | 5/2004 | Haller et al. |
| 2004/0104455 A1 | 6/2004 | Shimizu |
| 2004/0106919 A1 | 6/2004 | Hood |
| 2004/0136499 A1 | 7/2004 | Holland et al. |
| 2004/0181251 A1 | 9/2004 | Hacker et al. |
| 2004/0193150 A1 | 9/2004 | Sharkey et al. |
| 2004/0230190 A1 | 11/2004 | Dahla et al. |
| 2005/0065510 A1 | 3/2005 | Carmel et al. |
| 2005/0080407 A1 | 4/2005 | Ehr et al. |
| 2005/0228467 A1 | 10/2005 | Jiang |
| 2005/0234446 A1 | 10/2005 | Van Wyk et al. |
| 2005/0240229 A1 | 10/2005 | Whitehurst et al. |
| 2005/0277915 A1 | 12/2005 | De Cesare et al. |
| 2006/0122680 A1 | 6/2006 | Auth et al. |
| 2006/0153337 A1 | 7/2006 | Holland et al. |
| 2006/0184165 A1 | 8/2006 | Webster et al. |
| 2006/0212030 A1 | 9/2006 | McGaffigan |
| 2006/0217703 A1 | 9/2006 | Chornenky et al. |
| 2006/0224154 A1 | 10/2006 | Shadduck et al. |
| 2006/0235377 A1 | 10/2006 | Earley et al. |
| 2006/0259031 A1 | 11/2006 | Carmel et al. |
| 2006/0271109 A1 | 11/2006 | Kuzma et al. |
| 2006/0293653 A1 | 12/2006 | Van Wyk |
| 2008/0077129 A1* | 3/2008 | Van Wyk ............ A61B 18/149 606/46 |
| 2008/0121419 A1 | 5/2008 | Haller et al. |
| 2008/0131723 A1 | 6/2008 | Tucker et al. |
| 2008/0208189 A1 | 8/2008 | Van Wyk et al. |
| 2008/0269596 A1 | 10/2008 | Revie et al. |
| 2009/0069802 A1 | 3/2009 | Garito et al. |
| 2010/0015491 A1 | 1/2010 | Yamanis |
| 2010/0023000 A1 | 1/2010 | Stevenson et al. |
| 2010/0140330 A1 | 6/2010 | Chatterjee et al. |
| 2010/0152724 A1 | 6/2010 | Marion et al. |
| 2010/0160910 A1 | 6/2010 | Kramer et al. |

FOREIGN PATENT DOCUMENTS

| | | |
|---|---|---|
| GB | 2327352 | 1/1999 |
| WO | WO 2000/062685 | 10/2000 |
| WO | WO 2006/124624 | 11/2006 |

* cited by examiner

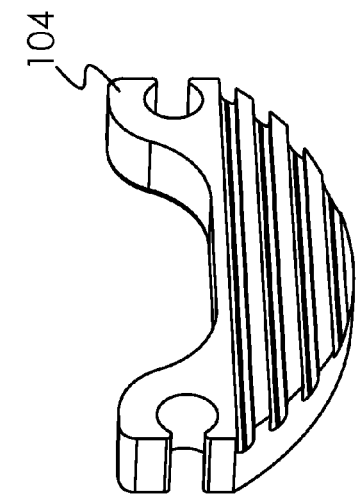
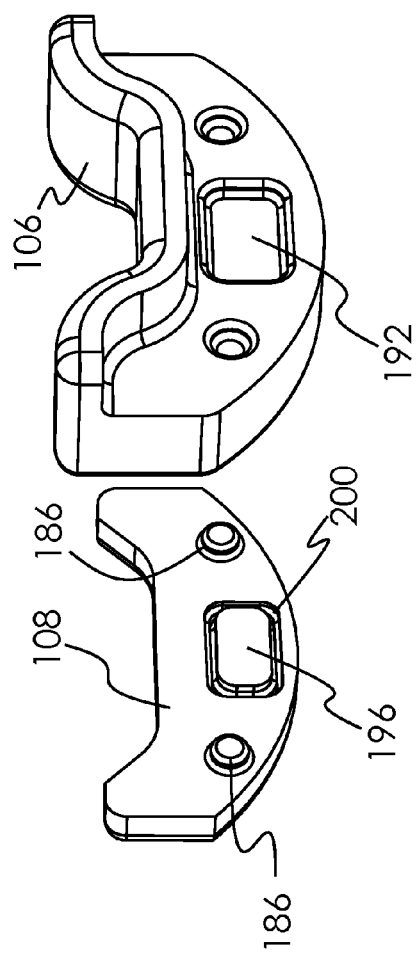
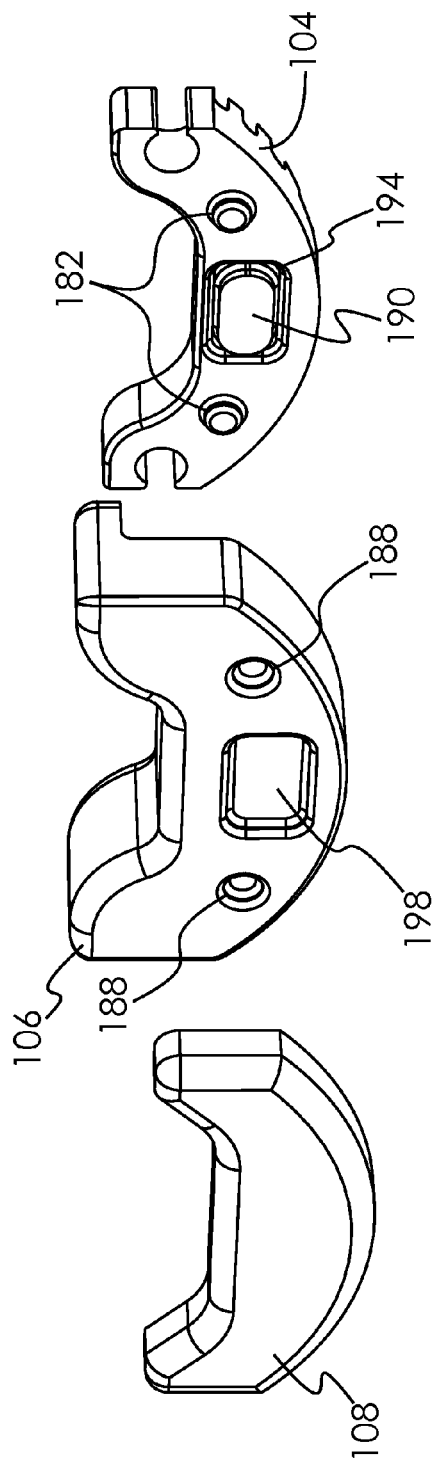

PLASMA RESECTION ELECTRODE

CROSS REFERENCE TO RELATED APPLICATION

This application claims the benefit of U.S. Provisional Patent Application No. 61/681,855, filed Aug. 10, 2012, which is hereby incorporated herein by reference in its entirety.

TECHNICAL FIELD OF THE DISCLOSURE

The present disclosure relates generally to the field of electrosurgery, and more particularly, to a plasma resection electrode.

BACKGROUND OF THE DISCLOSURE

As compared to conventional tissue removal techniques, electrosurgical procedures are advantageous in that they generally reduce patient bleeding and trauma. More recently, electro surgical devices have gained significant popularity due to their ability to accomplish outcomes with reduced patient pain and accelerated return of the patient to normal activities. Such instruments are electrically energized, typically using an RF generator operating at a frequency between 100 kHz to over 4 MHz.

Many types of electrosurgical devices are currently in use. They can be divided to two general categories—monopolar devices and bipolar devices. When monopolar electrosurgical devices are used, the RF current generally flows from an exposed active electrode, through the patient's body, to a passive, return current electrode that is externally attached to a suitable location on the patient body. In this manner, the patient's body becomes part of the return current circuit. In the context of bipolar electrosurgical devices, both the active and the return current electrodes are exposed, and are typically positioned in close proximity to each other (normally mounted on the same instrument). In bipolar procedures, the RF current flows from the active electrode to the return electrode through the nearby tissue and conductive fluids.

High frequency electrosurgical instruments, both monopolar and bipolar, have been used in the context of many surgical procedures in such fields as urology, gynecology, laparoscopy, general surgery, arthroscopy, ear nose and throat and more. In many fields of electrosurgery, monopolar and bipolar instruments operate according to the same principles. For example, the electrosurgical interventional instrument, whether monopolar or bipolar, may be introduced through an instrument such as a resectoscope, or alternatively directly to perform the needed surgical procedure in the target area of the patient's body. In some cases, an externally supplied liquid (often referred to as an "irrigant"), either electrically conductive or non-conductive, is applied. In other electrosurgical procedures, the instruments rely only on locally available bodily fluids, without requiring an external source of fluid. Procedures performed in this manner are often referred to as performed in "dry-field". When necessary, the electrosurgical instruments may be equipped with irrigation, aspiration or both.

Even though the benefits are well recognized, current electrosurgical instruments and procedures suffer from very significant deficiencies. For example, monopolar devices require the use of an additional external component, namely one or more grounding plates, remotely attached to a suitable location on the skin of the patient. Thus, in that monopolar devices require current to flow from the active electrode through the patient's body, they invariably allow for the possibility that some of the current will flow through undefined paths in the patient's body, particularly when the instrument is not properly designed and positioned.

Bipolar electrosurgical devices have their own inherent drawbacks, often resulting from the close orientation of the return and active electrodes. The return electrode necessarily has a small area and, as a result, can cause undesired tissue heating, coagulating or evaporation at its contact point with the patient's tissue due to the relatively high current densities present thereon. In addition, with the bipolar configuration, the close proximity of the active and return electrodes creates the danger that the current will short across the electrodes. For this reason, bipolar devices normally operate at relatively low voltage (typically 100 to 500 V) to decrease the chances that a spark will bridge the gap between the active and return electrodes.

Electrosurgical procedures which cut or vaporize tissue rely on generation of sparks in the vicinity of the active electrodes to vaporize the tissue. Sparking is often referred to as "arcing" within gaseous bubbles in liquid, or alternatively as plasmas. Operation at relatively low voltage, as is necessary with bipolar instruments, can lead to less efficient sparking, reduced efficiency of the instrument, undesirable overheating of nearby tissue, and longer procedure time. Moreover, the use of electrosurgical bipolar procedures in electrically conductive environments is inherently problematic. For example, many arthroscopic procedures require flushing of the region to be treated with saline, both to maintain an isotonic environment, to carry away process heat and debris, and to keep the field of view clear. The presence of saline, which is a highly conductive electrolyte, can also cause electrical shorting of a bipolar electrosurgical probe, thereby causing probe destruction and unintended and unnecessary heating in the treatment environment which, in turn, can result in unintended and uncontrolled tissue destruction.

In addition, current monopolar and bipolar instruments used to cut or vaporize tissue often do not have effective means for controlling bubbles, which is essential to the safety and efficiency of many procedures. As a result, the efficiency of the instruments is often low and the procedure length is increased. Electro surgical instruments that lack an effective means for trapping of bubbles include, for example, cutting loops, rollers, needles and knives, resection instruments and ablators. Furthermore, many current monopolar and bipolar instruments are not designed to take full advantage of either the electrical properties of the fluids present in the vicinity of the procedure site (bodily fluids, including blood, as well as irrigation fluids, either electrically conductive or non-conductive) or the electrical properties of the tissue itself.

Vaporizing electrodes (ablators) currently available for use in conductive liquids, whether monopolar or bipolar, have an active electrode surrounded by an insulator that is significantly larger in size than the ablating surface of the electrode. For ablators with a circular geometry, the diameter of the portion of the probe which generates ablative arcs (i.e., the "working" diameter) is generally not greater than 70 to 80 percent of the diameter of the insulator (i.e., the "physical" diameter). Accordingly, only about 50% of the physical probe area can be considered effective. This increases the size of the distal end of the electrode necessary to achieve a given ablative surface size, and necessitates the use of a cannula or other instrument, often with unnecessarily large lumens, an undesirable condition.

As noted above, it is well known in the prior art to use high frequency current in electrosurgical instruments, both monopolar and bipolar, introduced via an instrument such as a resectoscope, endoscope or directly, to perform the desired surgical procedure in such fields as urology, gynecology, laparoscopy, general surgery, arthroscopy, ear nose and throat and more. In fact, a number of radio frequency devices, both monopolar and bipolar, and techniques, both in conductive and non-conductive fluids, are described in the art for urological and gynecological purposes.

Endoscopic transurethral resection and/or thermal treatment of tissue is generally accomplished using a resectoscope, a device which allows the scope and other instruments to pass easily into the urethra. Resectoscopes are well known in the art. Various elongated probes are used to cut, vaporize, coagulate, or otherwise thermally treat tissue. For example, resectoscopes are often used in the treatment of benign pro static hyperplasia (BPH) or benign prostatic enlargement (BPE). BPH is a very common problem in western society and, if left untreated, can give rise to poor quality of life, urinary infection, bladder stones or even kidney failure. BPH is due to hormonal changes in the prostate and lifestyle of the patient, and is characterized by the enlargement or overgrowth of the gland as a result of an increase in the number of its constituent cells. BPH can raise PSA levels two to three times higher than normal. Men with increased PSA levels have a higher chance of developing prostate cancer. BPH usually affects the innermost part of the prostate first, and enlargement frequently results in a gradual squeezing of the urethra at the point where it runs through the prostate. The squeezing sometimes causes urinary problems, such as difficulty urinating. BPH may progress to the point of generating a dense capsule that blocks the flow of urine from the bladder, resulting in the inability to completely empty the bladder. Eventually, this can lead to bladder and kidney malfunction. Transurethral resection of the prostate (TURP) is the treatment of choice for BPH, and the most common surgery performed for the condition, using a resectoscope inserted through the urethra. Resectoscopes, along with their associated electrosurgical probes, are also used in various laparoscopic and gynecological procedures.

Endoscopic electro surgical probes of the type used with a resectoscope may be used with conductive or nonconductive irrigants. When conductive irrigants are used, current flows and/or arcing from any uninsulated portion of the active electrode which contacts the conductive fluid. Due to this reality, probes for use in conductive fluids must be insulated except for portions which will give the desired clinical effect during use. In a nonconductive fluid environment, conduction occurs only from portions of the active electrode which are in sufficiently close proximity to tissue to cause current flows and/or arcing between the electrode and the tissue, or from portions of the electrode which are in contact with tissue. During a surgical procedure, however, even non-conductive irrigants can achieve some level of conductivity, for example as a result of bodily fluids seeping from the patient's tissue into the irrigant. This contamination may increase the local conductivity to a degree sufficient to cause significant current flow from uninsulated portions of a probe designed for use in a non-conductive irrigant. Accordingly, it may be presumed that all fluids have some level of conductivity during laparoscopic electro surgery, and that all probes which are used partially or completely submerged in a liquid will benefit from a construction that maximizes electrode efficiency by maximizing the portion of the RF energy which provides clinical benefit.

Probes may be used for vaporization or for thermal modification, such as lesion formation. Vaporization occurs when the current density at the active electrode is sufficient to cause localized boiling of the fluid at the active electrode, and arcing within the bubbles formed. When the current density is insufficient to cause boiling, the tissue in proximity to the active electrode is exposed to high-temperature liquid and high current density. The temperature of the liquid and tissue is affected by the current density at the active electrode, and the flow of fluid in proximity to the electrode. The current density is determined by the probe design and by the power applied to the probe. Any given probe, therefore, can function as either a vaporizing probe or a thermal treatment probe, depending on the choice of the power applied to the probe. Lower powers will cause a probe to operate in a thermal treatment mode rather than in the vaporizing mode possible if higher power is applied.

The bubbles which form at the active electrode when a probe is used in vaporizing mode, form first in regions of the highest current density and lowest convection of the liquid. When they reach a critical size, these bubbles support arcing within and allow for vaporization of tissue. Bubbles also form in areas of lower current density as the conductive liquid in these regions reaches sufficient temperature. While these bubbles generally do not support arcing, they cover portions of the exposed electrode surface, thereby insulating these portions of the surface. This insulation of non-productive regions of the electrode decreases non-beneficial current flow into the liquid thereby allowing the electrode to achieve its clinically beneficial results at lower power levels. It is possible to increase electrode efficiency by managing these bubbles so as to retain them in regions in which their presence insulates the electrode.

In summary, the geometry, shape and materials used for the design and construction of electrosurgical instruments greatly affect the performance. Electrodes with inefficient designs will require substantially higher power levels than those with efficient designs. While currently available electrodes are capable of achieving desired surgical effects, they are not efficient for accomplishing these tasks and may result in undesired side effects to the patient.

SUMMARY OF THE DISCLOSURE

In view of the ever present need in the art for more efficient electrode design, the present disclosure relates to electro surgical devices having high efficiency and which may be readily used in combination with a resectoscope The disclosed embodiments are directed to an advanced, high efficiency, electrosurgical device designed for use with a resectoscope, and equipped with one or more additional metallic electrodes which are not connected directly to any part of the power supply circuit. This electrically unconnected electrode may contact the surrounding conducting liquid and/or tissue. The electrical potential of this disconnected electrode is "floating" and is determined by the size and position of the electrode, the tissue type and properties, and the presence or absence of bodily fluids or externally supplied fluid. In the context of the present invention, the "floating" electrode is preferably mounted in such a way that one portion of the electrode is in close proximity to the tip of the active electrode, in the region of high potential. Another portion of the floating electrode is preferably placed farther away, in a region of otherwise low potential. This region of low potential may be in contact with the fluid environment, in contact with tissue, or both.

In the context of the present invention, the floating electrode generates and concentrates high power density in the vicinity of the active region, and results in more efficient liquid heating, steam bubble formation, bubble trapping and arc formation in this region. This increases the probe efficiency, which, in turn, allows the surgeon to substantially decrease the applied RF power and thereby reduce the likelihood of patient burns and unintended local tissue injury. The probe may be operated so that the portion of the floating electrode in close proximity to the active electrode has sufficient current density to produce vaporization of the liquid and arcing so as to vaporize tissue. Alternatively, the probe may be operated so that the floating electrode contacts tissue, wherein those portions of the floating electrode in contact with the tissue have sufficient current density to thermally coagulate blood vessels and tissue. This is particularly useful for achieving hemostasis in vascular tissue.

The innovative electrosurgical devices with floating electrodes of the present invention may be very effective in other medical procedures, other than those involving tissue evaporation (ablation), including, for instance, for thermal tissue treatment, lesion formation, tissue sculpting, and coagulation.

Accordingly, in view of these noted needs and objectives, the present invention provides in one embodiment an electrosurgical instrument comprising:
  a conductive member having a member proximal end and a member distal end;
  an active electrode coupled to said member distal end, said active electrode comprising a proximal face that is v-shaped;
  a floating electrode, said floating electrode being electrically isolated from said conductive member; and
  an insulator disposed between said active electrode and said floating electrode.

In a further embodiment, the present invention provides an electrosurgical instrument comprising:
  a conductive member having a member proximal end and a member distal end;
  an active electrode coupled to said member distal end, said active electrode comprising:
    a proximal face;
    at least one first groove formed into said proximal face; and
    at least one second groove formed into said proximal face, said at least one second groove oriented in a different direction than said at least one first groove and forming at least one intersection therewith;
  a floating electrode, said floating electrode being electrically isolated from said conductive member; and
  an insulator disposed between said active electrode and said floating electrode.

In a further embodiment, the present invention provides an electrosurgical instrument comprising:
  a conductive member having a member proximal end and a member distal end;
  an active electrode coupled to said member distal end, said active electrode comprising a proximal face that is concave;
  a floating electrode, said floating electrode being electrically isolated from said conductive member; and
  an insulator disposed between said active electrode and said floating electrode.

In a further embodiment, the present invention provides an electrosurgical instrument, comprising:
  a conductive member having a member proximal end and a member distal end;
  an active electrode coupled to said member distal end, said active electrode comprising a proximal face that is convex;
  a floating electrode, said floating electrode being electrically isolated from said conductive member; and
  an insulator disposed between said active electrode and said floating electrode.

In a further embodiment, the present invention provides an electrosurgical instrument comprising:
  a conductive member having a member proximal end and a member distal end;
  an active electrode coupled to said member distal end, said active electrode comprising a proximal face, an opposite distal face, a first side joining said proximal face and said distal face, and a second side joining said proximal face and said distal face;
  a floating electrode, said floating electrode being electrically isolated from said conductive member; and
  an insulator disposed between said active electrode and said floating electrode, said insulator extending over at least a portion of said first and second sides.

In a further embodiment, the present invention provides an electrosurgical instrument comprising:
  a member having a member proximal end and a member distal end;
  an active electrode coupled to said member distal end, said active electrode having at least one coupler of a first sex thereon;
  a floating electrode, said floating electrode being electrically isolated from said conductive member; and
  an insulator disposed between said active electrode and said floating electrode, said insulator having at least one coupler of a second sex thereon;
  wherein said at least one coupler of a first sex mates with respective ones of said at least one coupler of a second sex.

In a further embodiment, the present invention provides an electrosurgical instrument comprising:
  a conductive member having a member proximal end and a member distal end;
  an active electrode coupled to said member distal end, said active electrode comprising at least one first hole formed therein;
  a floating electrode, said floating electrode being electrically isolated from said conductive member; and
  an insulator disposed between said active electrode and said floating electrode, said insulator comprising at least one second hole formed therein;
  wherein said member distal end extends through said at least one first hole and into said at least one second hole.

In a further embodiment, the present invention provides an electrosurgical instrument comprising:
  a conductive member having a member proximal end and a member distal end;
  an active electrode coupled to said member distal end, said active electrode comprising at least one first hole formed therein;
  a floating electrode, said floating electrode being electrically isolated from said conductive member; and
  an insulator disposed between said active electrode and said floating electrode, said insulator comprising at least one first protrusion formed thereon;
  wherein said at least one first protrusion extends into a respective one of said at least one first hole.

In a further embodiment, the present invention provides an electrosurgical instrument comprising:
  a conductive member having a member proximal end and a member distal end;

an active electrode coupled to said member distal end, said active electrode comprising a proximal face, an opposite distal face, a first side joining said proximal face and said distal face, and a second side joining said proximal face and said distal face;
a floating electrode, said floating electrode being electrically isolated from said conductive member; and
an insulator disposed between said active electrode and said floating electrode, said insulator extending over at least a first portion of said proximal face.

In a further embodiment, the present invention provides an electrosurgical instrument comprising:
a first conductive member having a first member proximal end and a first member distal end;
a second member having a second member proximal end and a second member distal end;
an active electrode coupled to said first member distal end;
a floating electrode coupled to said second member distal end; and
an insulator disposed between said active electrode and said floating electrode;
wherein said floating electrode is electrically isolated from said active electrode; and
wherein said second member is electrically isolated from said active electrode.

In a further embodiment, the present invention provides a kit for assembling an electro surgical instrument, the kit comprising:
a metal active electrode having an active electrode proximal face and an active electrode distal face, the active electrode distal face including a first protrusion surrounded by a first recess;
a metal floating electrode having a floating electrode proximal face and a floating electrode distal face, the floating electrode proximal face including a second protrusion surrounded by a second recess; and
a ceramic insulator having an insulator proximal face and an insulator distal face, the insulator proximal face including a third recess and the insulator distal face including a fourth recess;
wherein when said ceramic insulator is positioned between said active electrode and said floating electrode, the first protrusion mates with the third recess; and
wherein when said ceramic insulator is positioned between said active electrode and said floating electrode, the second protrusion mates with the fourth recess;
whereby braze bonding of said metal active electrode and said metal floating electrode to said ceramic insulator is facilitated.

In a further embodiment, the present invention provides an electrosurgical instrument comprising:
a conductive member having a member proximal end and a member distal end, wherein a first cross-sectional area of said member distal end is larger than a second cross-sectional area of said member proximal end;
an active electrode having an active electrode proximal face and an active electrode distal face, said active electrode further having a passage formed therethrough, said passage having recess at said active electrode distal face, said passage having a larger cross-sectional area at said active electrode distal face than at said active electrode proximal face;
a floating electrode, said floating electrode being electrically isolated from said conductive member; and
an insulator disposed between said active electrode and said floating electrode;
wherein said conductive member is disposed in said passage such that said member distal end is positioned within said recess.

In a further embodiment, the present invention provides an electrosurgical instrument comprising:
a member having a first member proximal end and a second member proximal end, said a first and second member proximal ends being joined at a member distal end;
an active electrode having an active electrode proximal face and an active electrode distal face, said active electrode further having a first passage formed therethrough and a second passage formed therethrough, said member passing through said first and second passages;
a floating electrode, said floating electrode being electrically isolated from said member; and
an insulator disposed between said active electrode and said floating electrode.

In another embodiment, the present invention provides an electrosurgical instrument comprising:
a conductive member having a member proximal end and a member distal end;
an active electrode coupled to said member distal end;
a floating electrode, said floating electrode being electrically isolated from said conductive member;
an insulator disposed between said active electrode and said floating electrode; and
a dielectric shield disposed over a first portion of said active electrode and a second portion of said conductive member, said dielectric shield having a melting point high enough to prevent the dielectric shield from melting when the active electrode is energized.

In another embodiment, the present invention provides an electrosurgical instrument comprising:
a conductive member having a member proximal end and a member distal end;
an active electrode coupled to said member distal end;
a floating electrode, said floating electrode being electrically isolated from said conductive member;
an insulator disposed between said active electrode and said floating electrode; and
a dielectric shield disposed over a first portion of said conductive member, said dielectric shield having a melting point high enough to prevent the dielectric shield from melting when the active electrode is energized.

In the context of the present invention, the electrosurgical device herein disclosed may take the form of a probe for use with a resectoscope, wherein the probe has an elongated proximal portion and an active distal portion, the distal portion having at its distal end at least one active electrode and at least one floating electrode. The active electrode is preferably connected via cabling disposed within the elongated proximal portion to an externally disposed electrosurgical generator. At least a portion of the distal-most portion of at least one floating electrode may be positioned in close proximity to at least one active electrode. In one embodiment, the active electrode has an ablating surface (often referred to herein as the "active surface" or "working surface") composed of an array of raised and recessed regions particularly configured to maximize bubble retention and concentrate power density. The array may take the form of, for example, a plurality of walls and grooves, a plurality of elevated pins, a plurality of bumps and pockets, or a combination thereof. So long as the array performs the desired function (e.g., bubble retention, power density concentration), the specific design, geometry, arrangement and configuration of the array or its components is not particularly limited. For example, the array be continuous or discontinuous, evenly or unevenly spaced, composed of raises and recesses that are linear or non-linear (e.g., curvilinear, wavy, zigzagged, angled, etc.), parallel or circumferential positioned, or the like. In one embodiment, the array is composed of a plurality of grooves etched into the ablating surface of the active electrode, such grooves being of a depth and width for maximal retention of bubbles within the grooves.

The present invention also provides electrosurgical methods which utilize radio frequency (RF) energy to cut, resect, ablate, vaporize, denaturize, coagulate and form lesions in soft tissues, for example, in the context of urological, gynecological, laparoscopic, arthroscopic, and ENT procedures. In an illustrative embodiment, the present invention provides a method of treating benign prostatic hyperplasia (BPH) in a subject in need thereof.

These and other objects and features of the invention will become more fully apparent when the following detailed description is read in conjunction with the accompanying figures and examples. However, it is to be understood that both the foregoing summary of the invention and the following detailed description are of several various embodiments, and not restrictive of the invention or other alternate embodiments of the invention.

BRIEF DESCRIPTION OF THE FIGURES

FIGS. 32*a-c* are an exploded front perspective view of a nineteenth embodiment electrosurgical probe constructed in accordance with the principles of this invention.

FIGS. 33*a-c* are an exploded rear perspective view of the nineteenth embodiment electrosurgical probe illustrated in FIGS. 32*a-c*.

DETAILED DESCRIPTION OF THE DISCLOSED EMBODIMENTS

Figure 1:
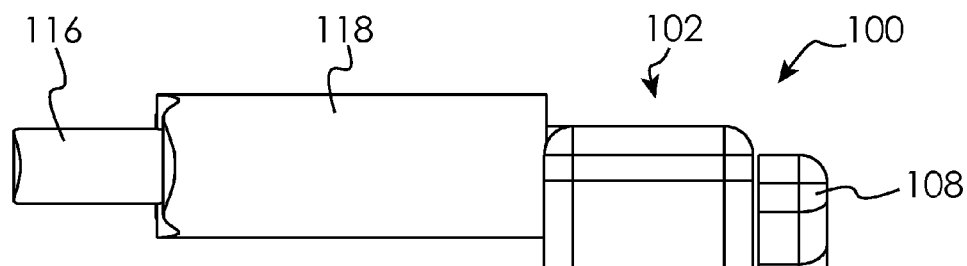
FIG. 1 is a top view of a first embodiment electrosurgical probe constructed in accordance with the principles of this invention.
Figure 2:
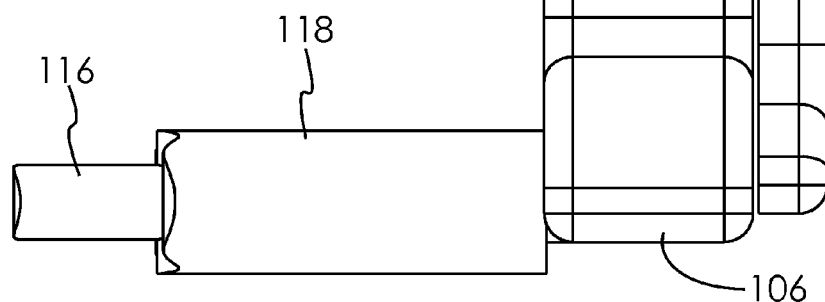
FIG. 2 is a side view of the electro surgical probe of FIG. 1.
Figure 3:
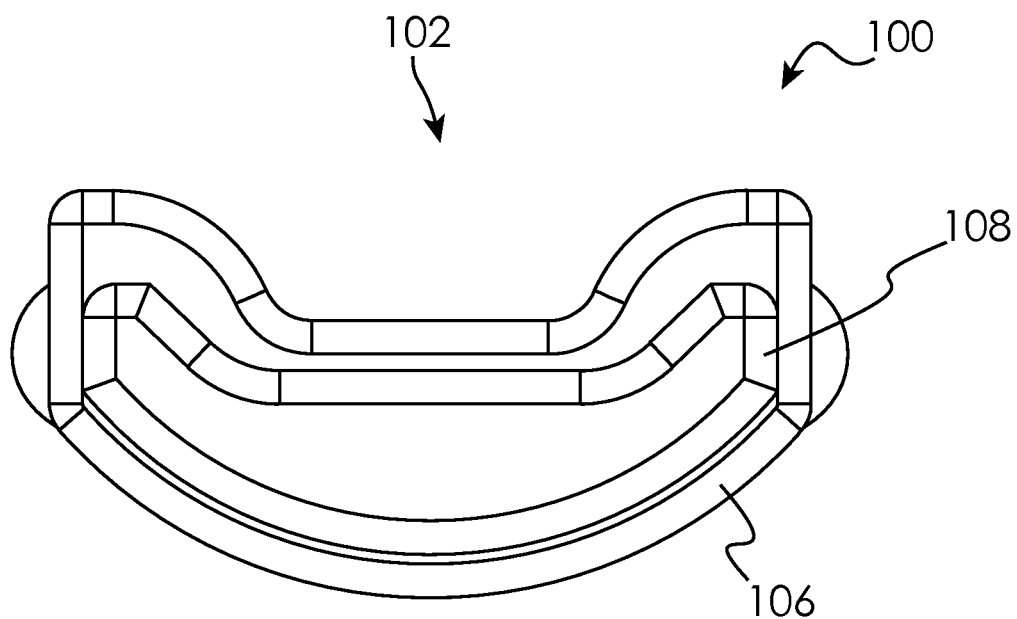
FIG. 3 is a distal end view of the electro surgical probe of FIG. 1.

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended, and alterations and modifications in the illustrated systems, and further applications of the principles of the disclosure as illustrated therein are herein contemplated as would normally occur to one skilled in the art to which the disclosure relates.

In the context of the present disclosure, the following definitions apply:

The words "a", "an", and "the" as used herein mean "at least one" unless otherwise specifically indicated.

In common terminology and as used herein, the term "electrode" may refer to one or more components of an electrosurgical device (such as an active electrode or a return electrode) or to the entire device, as in an "ablator electrode" or "cutting electrode". Such electrosurgical devices are often interchangeably referred to herein as "probes" or "instruments".

The term "proximal" refers to that end or portion which is situated closest to the user; in other words, the proximal end of the electro surgical device of the instant disclosure will typically comprise the handle portion.

The term "distal" refers to that end or portion situated farthest away from the user; in other words, the distal end of the electro surgical device of the instant disclosure will typically comprise the active electrode portion.

The disclosed embodiments have both human medical and veterinary applications. Accordingly, the terms "subject" and "patient" are used interchangeably herein to refer to the person or animal being treated or examined. Exemplary animals include house pets, farm animals, and zoo animals. In certain embodiments, the subject is a mammal.

Unless otherwise defined, all technical and scientific terms used herein have the same meaning as commonly understood by one of ordinary skill in the art to which this invention belongs. In case of conflict, the present specification, including definitions, will control.

As noted above, the present disclosure is directed to high efficiency monopolar or bipolar electrosurgical devices and methods which utilize radio frequency (RF) energy to cut, resect, ablate, vaporize, denaturize, coagulate and form lesions in soft tissues, having particular utility in the context of urological (for example, in the treatment of BPH and bladder tumors), gynecological, laparoscopic, arthroscopic, and ENT procedures. The presently disclosed embodiments offer the following advantages when used in the treatment of BPH:

1. Efficacious tissue removal in conductive (e.g. isotonic saline, etc.) as well as non-conductive (e.g. glycine, manitol, etc.) irrigating fluid.
2. Reduced risk of transurethral resection (TUR) syndrome due to the ability to operate in isotonic saline.
3. Less need for speed during the operation due to (2) above, allowing more time to complete the procedure and ensure acceptable hemostasis.
4. Simultaneous coagulation during tissue vaporization, providing better control of bleeding than conventional RF electrosurgical electrodes.
5. Better choice for high-risk patients on anti-coagulation medicine who require long resection surgery.
6. Lower operating power required to vaporize tissue than prior art monopolar ball electrodes relying on heat. By applying less power and heat, the extent of thermal penetration into surrounding tissue is reduced, thus minimizing necrosis and inflammation, potentially speeding recovery time in the hospital.
7. The devices can be used with standard operating room equipment.
8. No tissue chips to be extracted following transurethral vaporization of the prostate.

At its most basic, the device of the present invention is comprised of electrosurgical probe having a conductive metallic electrode. This exposed electrode is referred to herein as the "active element" or "active electrode" of the probe. When placed into conductive liquid-tissue media and energized, the probe induces electrical current in the conducting liquid and nearby tissue. This current deposits energy into the liquid and tissue, thereby raising the local temperature and creating the desired clinical effect. The highest energy deposition occurs in areas closely proximate to the active tip where current density is largest.

Power density in close proximity to the tip depends primarily on the applied power, the shape and size of the exposed portion of the electrode, the surrounding liquid/tissue electrical conductivity, as well as the presence of bubbles. In the sparking regime, the power density also depends on the spark distribution and conductivity (i.e., the plasma conductivity). It is further affected by the size, shape, and position of the return current electrode. In most cases, positioning the return electrode in closer proximity to the active electrode increases the power density in the region near the electrode tip.

In the case of a monopolar probe, the return current is collected by a large return electrode (sometimes called dispersive electrode or return pad) placed on the patient's body, remote from the probe tip. The power concentration capability of a monopolar probe is determined by the shape of the exposed electrode: the smaller and sharper the tip is, the better its power concentration capability.

In the case of bipolar probes, the return current electrode is placed in moderate proximity to the active electrode (generally from 1 to 10 mm). In comparison with a monopolar probe having an active electrode of approximately the same shape, some additional power concentration takes place. The power concentration capability can be further controlled by the shape and position of the return electrode. Decreasing the distance between the return electrode and the active electrode increases the power concentration. A problem arises when the probe is generating sparks. (Recall that this is the goal of probe operation in ablation-tissue evaporation or cutting, for example). If the return electrode is placed sufficiently close to the tip to achieve a substantial increase of power concentration, the breakdown (arcing within bubbles) takes place between the tip and return electrode. The spark conductive channel connects the active electrode to the return current electrode and the power supply is loaded directly by the spark. Usually this leads to an extra high-energy deposition in the spark between metallic electrodes, thereby resulting in localized melting and vaporization of the electrodes themselves. In turn, this results in shorting of the power supply and destruction of both the active and return electrodes with little clinical benefit to the patient.

A good bipolar probe design must therefore avoid arcing between the active and return electrodes. Usually this is achieved by placing the return electrode a sufficiently large distance away from the active electrode to prevent direct breakdown between electrodes. Nevertheless, periodic arcing may take place such that both electrodes are eroded and eventually destroyed, especially in an aggressive mode of operation. Therefore, the additional degree of power concentration achievable by bipolar probes is severely limited.

In contrast, the electro surgical device of the present disclosure has one or more additional metallic electrodes which are not connected directly to any part of the power supply circuit, and therefore are called "floating". These floating electrodes are in contact with the tissue and/or liquid in proximity to the active electrode. The electrical potential of these additional electrodes is not fixed, but rather is "floating" and is determined by size and position of the electrode and the electrical conductivity of the tissue and/or liquid surrounding the distal end of the device. This floating electrode is positioned in such a way that one end of the floating electrode is in close proximity to the active electrode. Another portion of the floating electrode is positioned in a region of low potential in the liquid and/or tissue. The addition of this floating electrode thereby substantially modifies the electrical field distribution, and energy deposition, in the vicinity of the active electrode without the possibility of electrode destruction since the floating electrode is not directly connected to the electrical power supply.

The floating electrode therefore serves to concentrate the electric field in the region of the active electrode, but it does not provide a current path back to the RF generator that powers the electrosurgical device. In monopolar electrosurgical devices, there is an additional dispersive return electrode that is in contact with a remote portion of the patient's body and is coupled to the RF generator in order to complete the return path. In bipolar electrosurgical devices, there is a return electrode mounted near the active electrode near the distal end of the device, and this return electrode is coupled to the RF generator in order to complete the return path to ground. In either configuration, a floating electrode may be used to shape the electric field near the active electrode; however, the floating electrode should not be confused with the return electrode, as the floating electrode has no connection to the RF generator and is, in fact, isolated from the electrical circuit of the device.

In the absence of sparking (arcing within bubbles), the "floating" electrode increases power density in the vicinity of the probe tip. This is because the floating electrode extends from a high potential region (near the active electrode), to a region with low potential (farther from the active electrode), and "shorts" these points together. The probe's floating potential will be between the potentials of these points. The presence of the electrode decreases the potential near the active electrode, and thereby increases the electric field, current and power density in the region near the active electrode. A floating electrode works about the same way as any extended conductive object in an electrostatic field. The higher power density results in more efficient liquid heating and steam bubble formation, which, in turn, allows one to decrease the power applied to probe for a given effect. In the presence of the "floating" electrode, more sparks are generated in the active region, since this region is larger. Bubble trapping (the retention of bubbles in selected areas to insulate these areas for improved ablator efficiency) is greatly enhanced with proper design of the floating electrode, insulator and the active electrode.

Sparks are an active element of the electrosurgical process. A spark is generated in a steam bubble if the electrical field in the bubble (voltage difference across a bubble) is sufficient for dielectric breakdown. Usually sparks are generated in bubbles that are close to the active electrode of the probe because current density and field intensity are largest in this region.

The breakdown or spark inside a bubble is an electrically conductive channel of partly ionized pressurized gas. This medium is called highly collisional plasma. The basic property of this plasma is that the conductivity is proportional to the plasma density. Higher plasma temperatures are associated with higher ionization rates, plasma densities and conductivity.

Usually, energy is deposited into highly collisional plasmas by electric current driven by voltage applied to electrodes at the ends of a plasma channel. In the case of a plasma channel formed inside of a bubble, the inner parts of the bubble surface having the largest voltage difference act as the "electrodes" to which the channel is connected. More frequently, but not always, one of these electrodes is a metallic surface of the active electrode and the other is the opposite surface of the bubble or the surface of the tissue.

Electrically, the plasma channel is characterized by its impedance. The efficiency of energy deposition strongly depends on the ratio between the plasma channel impedance and the power supply impedance. Efficiency (the portion of applied energy deposited to the plasma) as high as 50% can be achieved for matched conditions in which the power supply impedance equals the spark (plasma channel) impedance. If the channel impedance is too large or too small, the power deposition in the plasma is decreased.

As described previously herein, the additional "floating" electrode can significantly increase the energy density in the region surrounding the active electrode. This makes it possible to substantially increase the power deposited into the spark. Since the floating electrode can be placed very close to the probe tip, the largest probability is for breakdown and plasma channel formation in the region between the two electrodes—the active electrode and the floating electrode. The plasma channel current can now be supported not by a bubble size fraction of the induced current, but by a much larger volume of current flow that is determined by the size of the floating electrode. This floating electrode additionally concentrates current delivered to the spark. The optimum spark current can be controlled by adjusting the size and position of the floating electrode. Arcing, then, can occur through bubbles between the active and floating electrodes, or from either electrode through bubbles in contact with that electrode.

In summary, the presently disclosed embodiments provide an advanced, electrosurgical probe equipped with one or more "floating electrodes" coupled with one or more active electrodes uniquely designed and configured for tissue treatment, including tissue ablation and vaporization, preferably in combination with a resectoscope.

A method of the present invention includes the step of positioning the electrosurgical probe adjacent to target tissue at a surgical site so that at least one of the active electrodes and at least a portion of at least one of the floating electrodes are in close proximity to the target tissue. Conductive or non-conductive irrigant may be supplied to the probe distal tip in the region between the active electrode(s) and the target tissue, and between the portion of the floating electrode in close proximity to the tissue, and the target tissue itself. Other portions of the floating electrode(s) may be in contact with target tissue, adjacent tissue, or fluid environment. Vacuum may be supplied via means within the elongated distal portion to the probe distal tip so as to remove excess irrigant as well as ablation products. The probe is energized, producing high current density and arcing in portions of the active electrode and floating electrode in close proximity to the target tissue. Lower density current flow from regions of the floating electrode(s) in contact with adjacent target tissue results in desiccation of the adjacent tissue so as to achieve hemostasis. While energized, the probe may be moved across the target tissue with a brushing or sweeping motion, or intermittently energized for a brief period of time and repositioned so as to affect the target tissue. When used with a resectoscope, the probe may be extended axially, energized and retracted proximally so as to cut a groove in the tissue. The process may be repeated until the desired volume of tissue is removed. The movement of the probe relative to the tissue may be manually achieved or alternatively automated.

The currently disclosed embodiments are also useful for medical procedures in which tissue is thermally treated rather than removed by vaporization, such as, for instance, cardiology, oncology and treatment of tumors, a process sometimes referred to as lesion formation for coagulation and/or denaturing of tissue. In these applications, the device is brought into close proximity, or contact, with tissue with or without the presence of externally applied irrigant at the site for thermal treatment. The voltage applied to the active electrode is reduced to a level which produces current densities insufficient for forming sparks and the associated bubbles. Tissue is heated to a desired temperature for a predetermined time sufficient for lesion formation. The floating electrode intensifies the electric field in the region surrounding the active electrode so as to produce a larger, more controlled and more uniform lesion.

EXAMPLES

Hereinafter, the present invention is described in more detail by reference to the exemplary embodiments. However, the following examples only illustrate aspects of the invention and in no way are intended to limit the scope of the present invention. As such, embodiments similar or equivalent to those described herein can be used in the practice or testing of the present invention.

In many of the disclosed embodiments, the electrodes may be incorporated into shafts which facilitate attachment of the electrode assembly to a resectoscope. Many styles of resectoscope are known in the art, and the configuration of the shaft may be as desired in order to interface with the desired resectoscope design. The shafts further conduct power to the active electrode. The shaft may receive power through the resectoscope from any general purpose RF electrosurgical unit commonly available in operating rooms, as is known in the art.

90 Degree Tip Configuration

Figure 6:
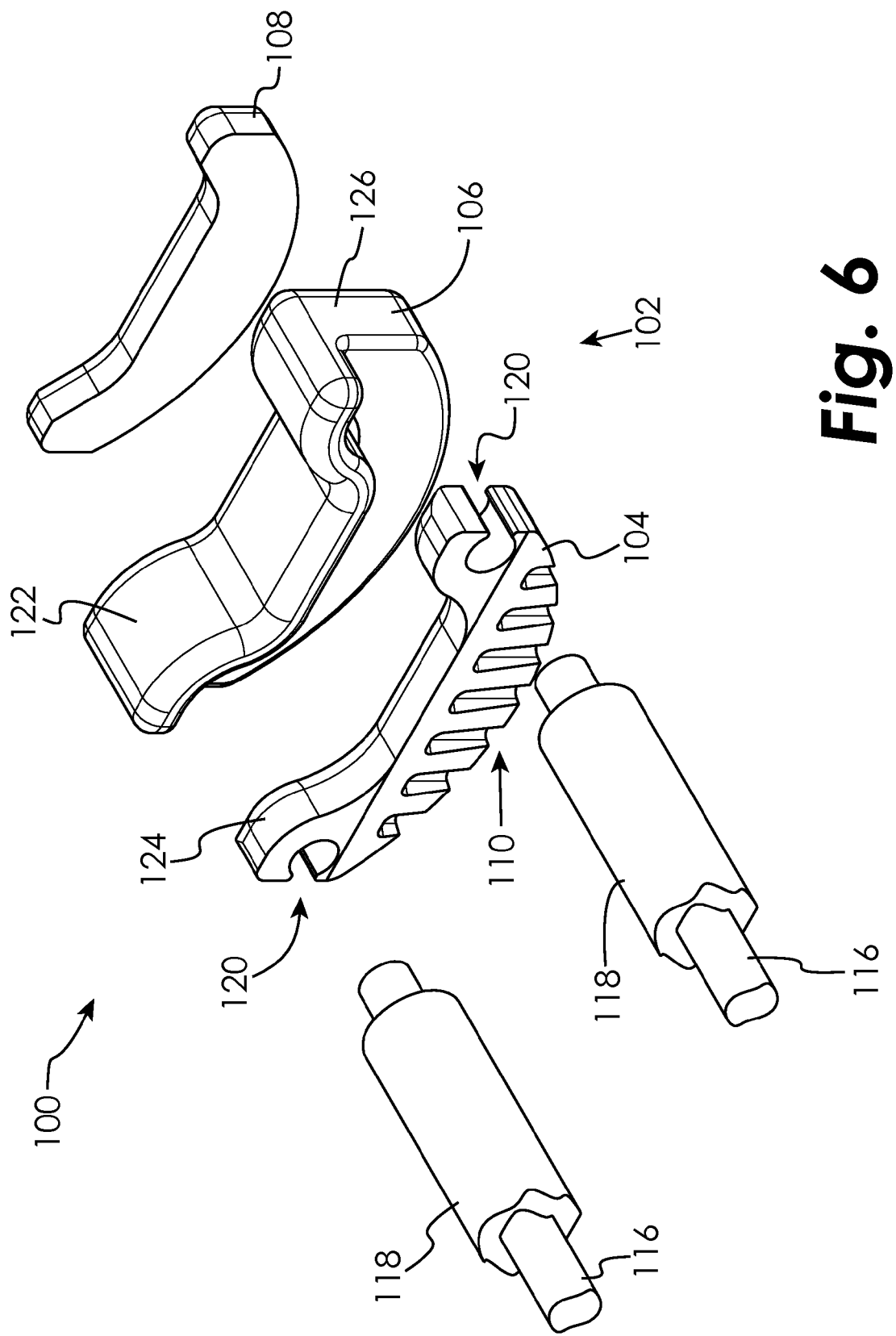
FIG. 6 is an exploded perspective view of the electro surgical probe of FIG. 1.

In one embodiment, the electrosurgical probe tip is oriented at an approximate 90 degree angle to the longitudinal axis Y (see FIG. 4) of the resectoscope. Referring now to FIGS. 1-6, which depict the distal-most portion of probe 100, referred to herein as the active head, electrode assembly 102 includes active electrode 104, insulator 106 and floating electrode 108. Active electrode 104 has a plurality of grooves 110 of width 112 and depth 114, width 112 and depth 114 being selected to trap bubbles in the grooves. However, the present invention is not limited to the grooved design depicted but encompasses any active electrode ablating surface specifically configured to maximize bubble retention and concentrate power density. So long as the ablating surface performs the desired function (e.g., bubble retention, power density concentration), the specific design, geometry, arrangement and configuration of the array or its components is not particularly limited. Accordingly, the ablating surface may be composed of an array of raised and recessed regions, e.g., a plurality of walls and grooves, a plurality of elevated pins, a plurality of bumps and pockets, or a combination thereof. As noted previously, the array be continuous or discontinuous, evenly or unevenly spaced, composed of raises and recesses that are linear or non-linear (e.g., curvilinear, wavy, zigzagged, angled, etc.), parallel or circumferential positioned, or the like. The grooves 110 increase the surface area in contact with the irrigating fluid to assist in bubble formation and also provide edges having high power density for electrical arcing to the surrounding tissue. The dimensions of the grooves are selected to trap bubbles in the grooves in order to increase the level of plasma formation. Active electrode 104 and floating electrode 108 are preferably formed from a suitable metallic material, examples of which include, but are not limited to, stainless steel, nickel, titanium, tungsten, molybdenum, and the like. Members 116, insulated by dielectric shields 118, are affixed to recesses 120 of active electrode 104 such that electrical power may be conducted by members 116 to active electrode 104. Insulator 106 and shields 118 are preferably formed from a suitable dielectric material having a melting point high enough to prevent melting when the active electrode 104 is energized during use. Examples of suitable materials for insulator 106 and shields 118 include, but are not limited to, alumina, zirconia, and high-temperature polymers. Members 116 are operably connected to a suitable RF generator for powering the active electrode 104. As best seen in FIG. 6, insulator 106 has a first portion 122 which insulates top surface 124 of active electrode 104, and a second portion 126 which electrically isolates floating electrode 108 from active electrode 104. When viewed axially in the distal direction as in FIG. 5, floating electrode 108 and second portion 126 of insulator 106 are flush with, or recessed behind active electrode 104.

Figure 4:
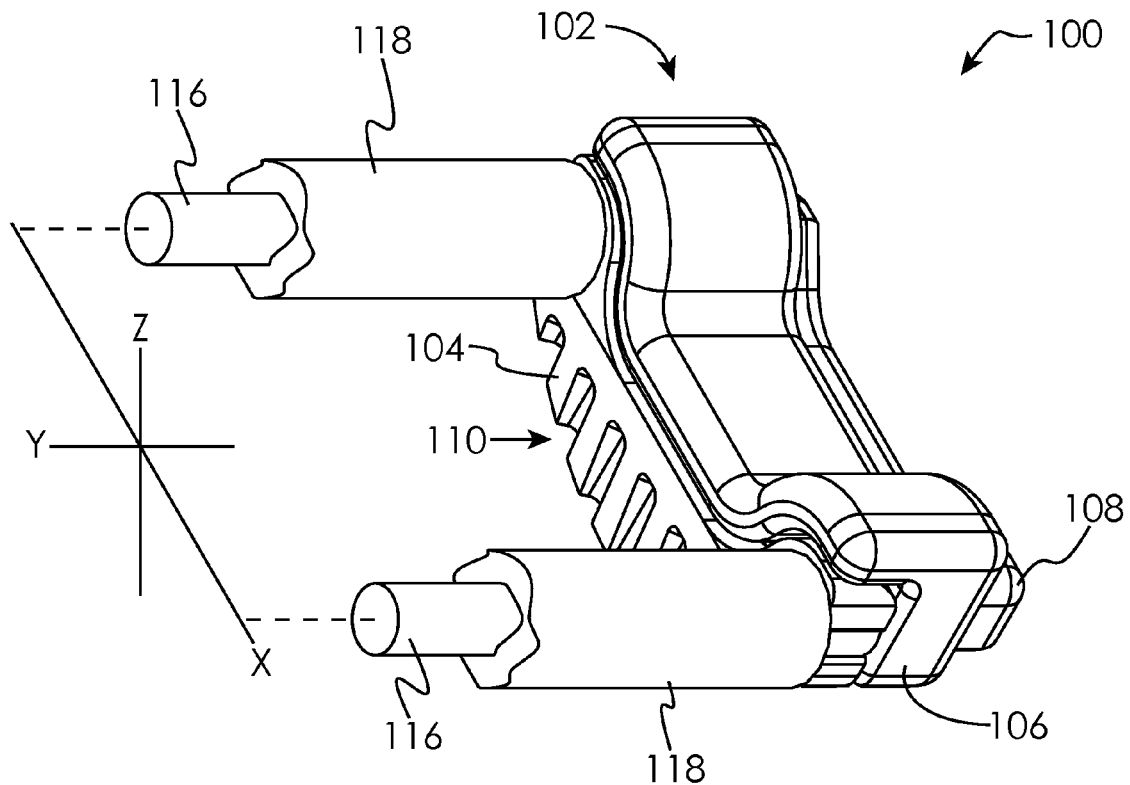
FIG. 4 is a perspective view of the electro surgical probe of FIG. 1.
Figure 5:
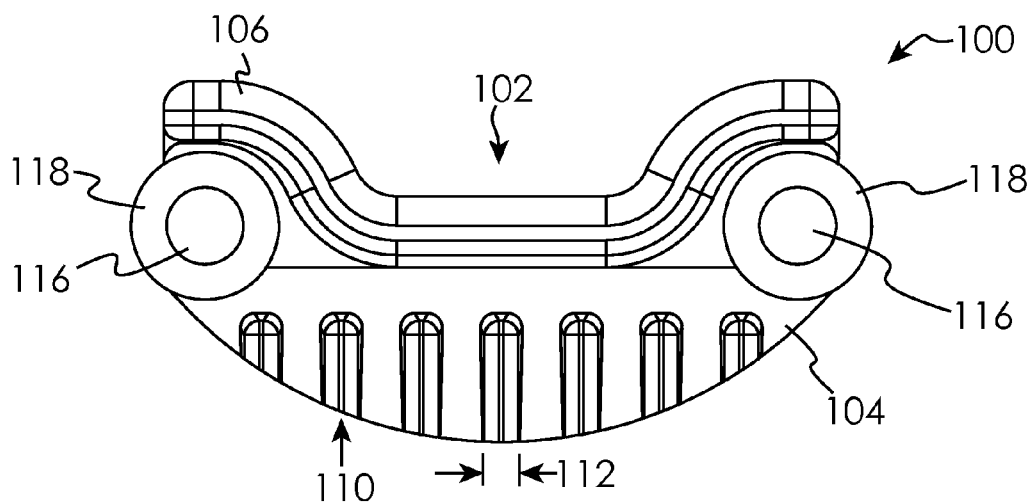
FIG. 5 is a proximal end view of the electrosurgical probe of FIG. 1.

Active electrode 104 incorporates a series of grooves 110 that facilitate entrapment of bubbles and plasma formation. With reference to FIG. 4, all points on the electrode assembly 102 are designed to be moved substantially in or parallel to the plane containing the axes X and Y, with the electrode assembly 102 reciprocating in directions coinciding with or parallel to the axis Y. The grooves 110 of the active electrode 104 have longitudinal axes that are in or parallel with the plane containing the axes X and Z (i.e. they are perpendicular to the plane containing the axes X and Y). Grooves 110 oriented in such a direction are referred to herein as vertical grooves. The present disclosure also contemplates horizontal grooves that are oriented substantially 90 degrees from the orientation of the vertical grooves, as well as grooves oriented at angles intermediate thereto.

Alternate Face Profile and Groove Configurations

Figure 7:
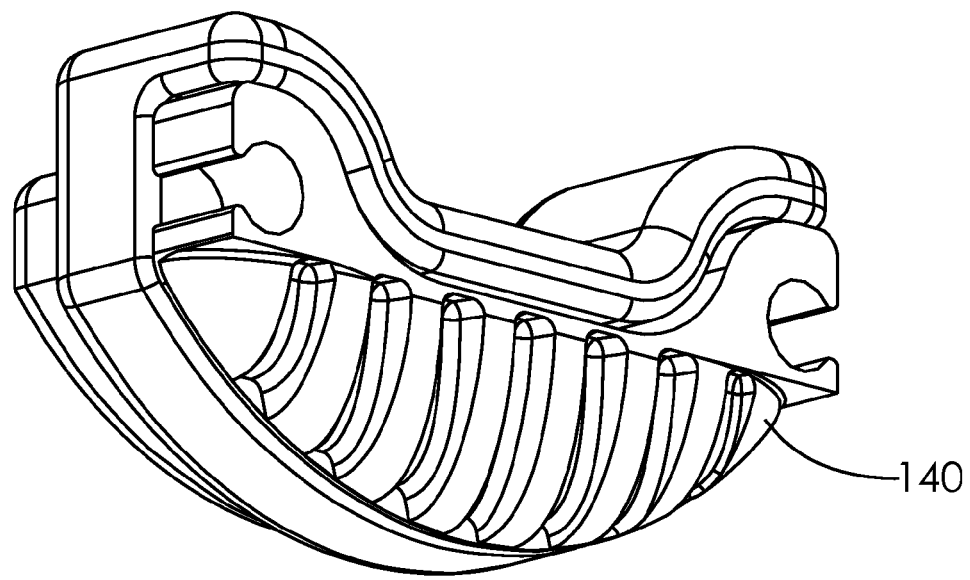
FIG. 7 is a perspective view of a second embodiment electrosurgical probe constructed in accordance with the principles of this invention.
Figure 8:
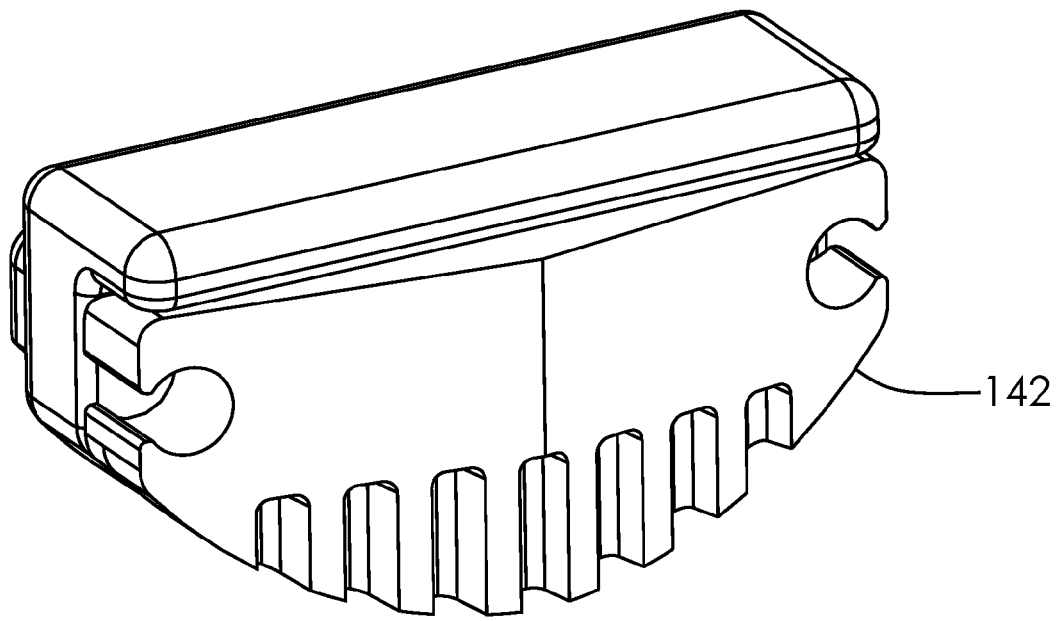
FIG. 8 is a perspective view of a third embodiment electrosurgical probe constructed in accordance with the principles of this invention.
Figure 9:
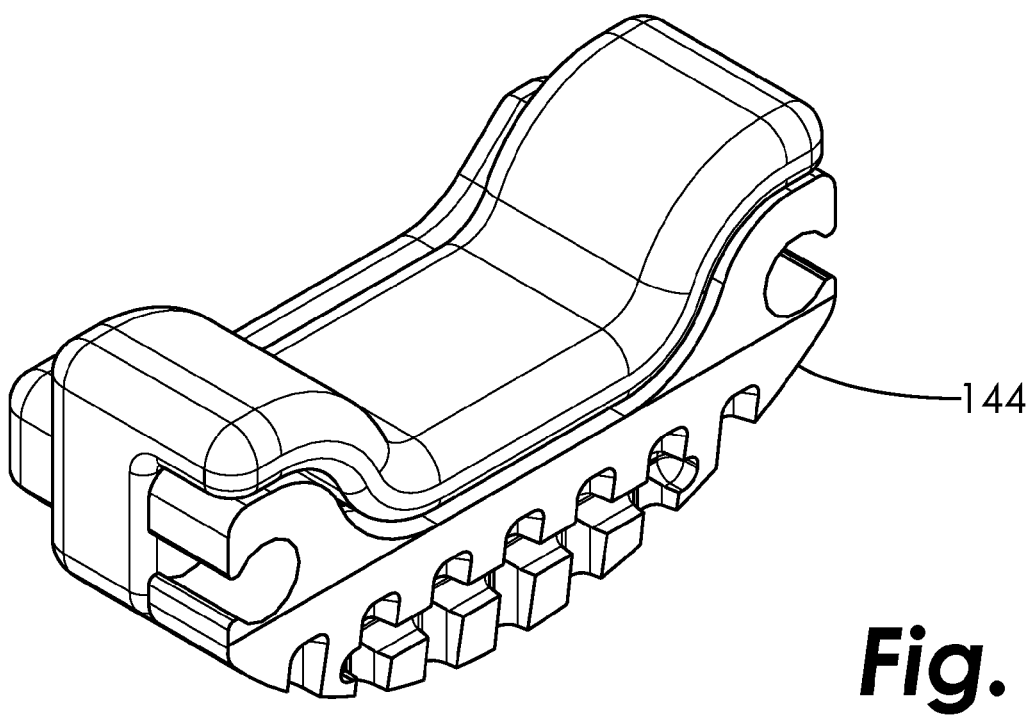
FIG. 9 is a perspective view of a fourth embodiment electro surgical probe constructed in accordance with the principles of this invention.
Figure 10:
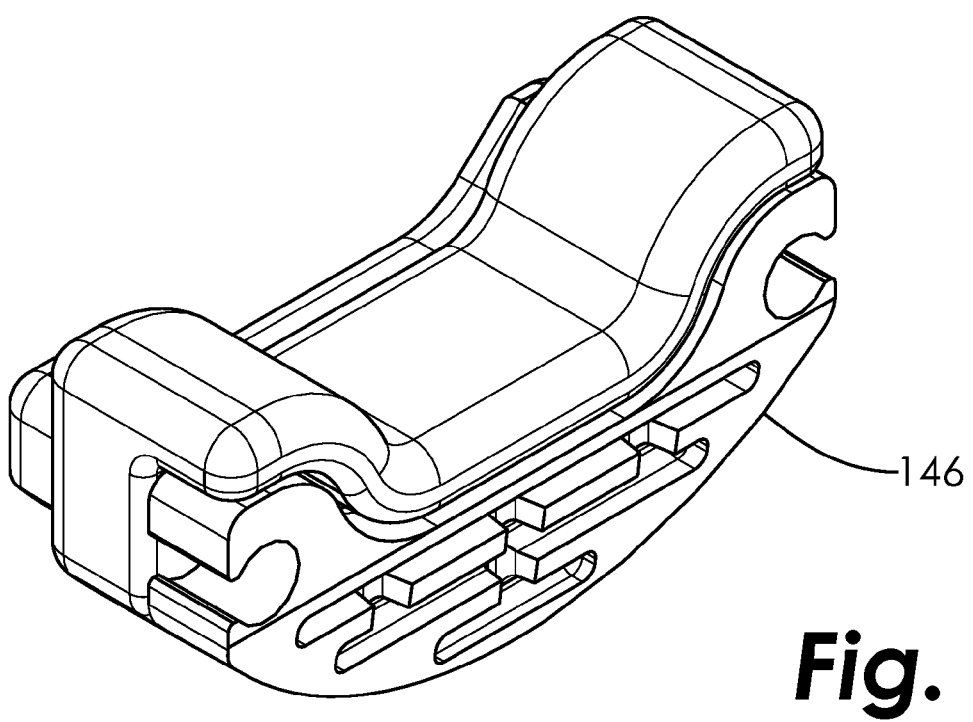
FIG. 10 is a perspective view of a fifth embodiment electrosurgical probe constructed in accordance with the principles of this invention.

As illustrated in FIGS. 1-6, the active electrode 104 has a substantially flat proximal face into which vertical grooves 110 are formed. As shown in FIG. 7, it is also contemplated that an active electrode 140 may be provided in which the proximal face is convex or domed. As shown in FIG. 8, an active electrode 142 may be provided in which the proximal face is v-shaped. As shown in FIGS. 9 (active electrode 144) and 10 (active electrode 146), a combination of intersecting vertical and horizontal grooves can be used to create corners at the intersections that concentrate the electric field density and thereby increase arcing efficiency. Although vertical and horizontal orthogonal grooves are illustrated, it will be appreciated that grooves oriented at different angles with respect to the plane of the device and with respect to the other grooves are also comprehended by the present disclosure.

Figure 11:
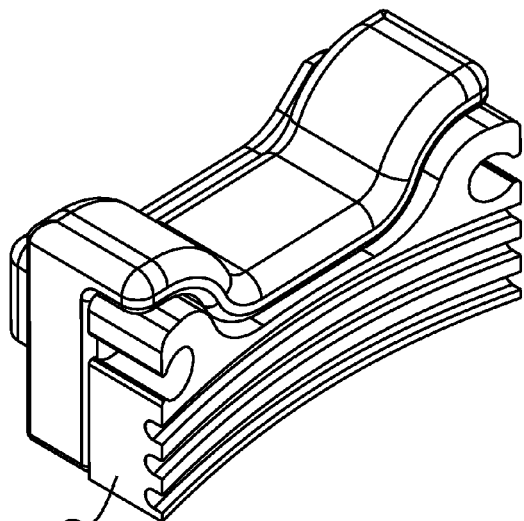
FIG. 11 is a perspective view of a sixth embodiment electrosurgical probe constructed in accordance with the principles of this invention.

As shown in FIG. 11, an active electrode 148 may have a proximal face that is concave in order to create a pocket that promotes bubble entrapment at the surgical site. Although active electrode 148 is illustrated with horizontal grooves, it will be appreciated that vertical grooves or grooves formed at intermediate angles, or a combination of such grooves, may also be used.

Figure 12:
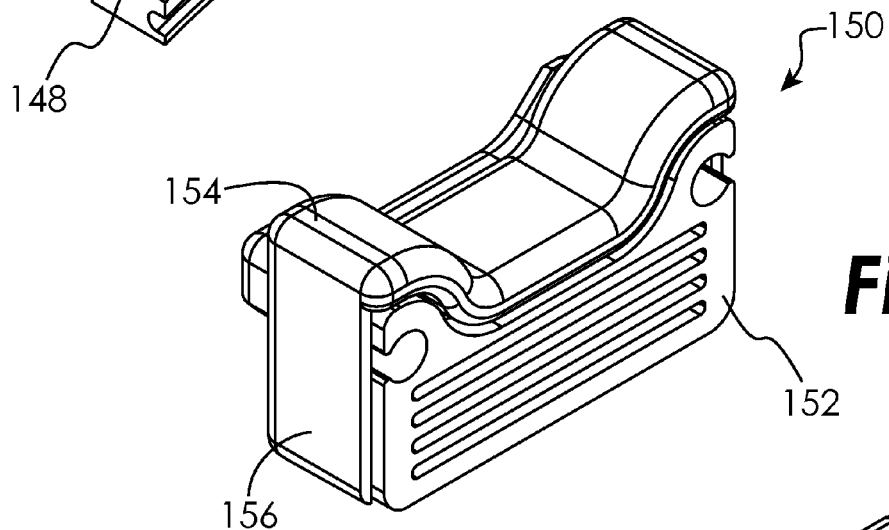
FIG. 12 is a perspective view of a seventh embodiment electrosurgical probe constructed in accordance with the principles of this invention.
Figure 13:
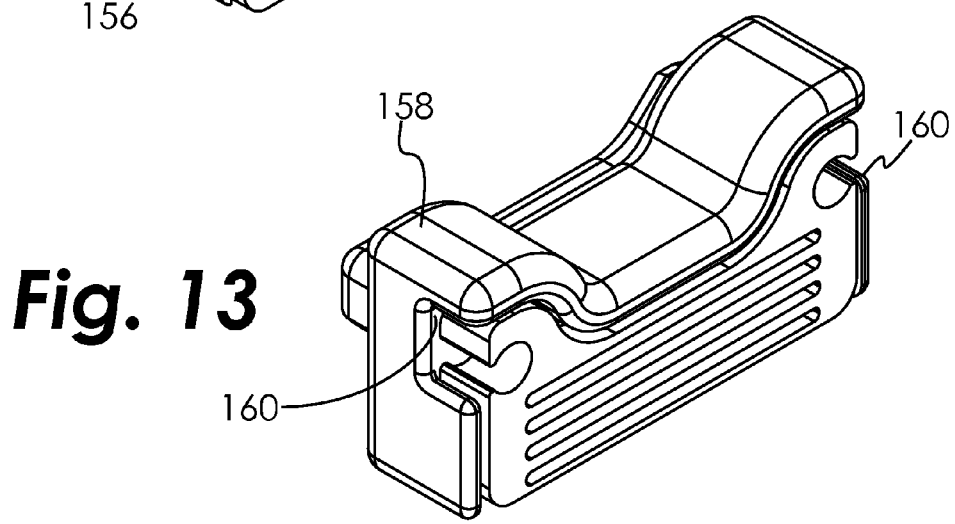
FIG. 13 is a perspective view of an eighth embodiment electrosurgical probe constructed in accordance with the principles of this invention.

FIG. 12 shows an electrode assembly 150 having an active electrode 152 that is received into a recess formed in insulator 154 by the provision of sidewalls 156. In an alternative embodiment shown in FIG. 13, the insulator 158 includes open areas 160 within the sidewalls to facilitate construction of the electrode assembly.

Manufacturing of the Electrode Assembly

Electrode assembly 102 of probe 100 (as well as the alternative embodiments disclosed herein) has a simple construction which may be produced at low cost. The following are offered as non-limiting examples only. Other forming and assembly methods will be apparent to those skilled in the art. Active electrode 104 may be formed by machining using wire Electrical Discharge Machining (EDM) and conventional machining, or by Metal Injection Molding (MIM). Floating electrode 108 may be formed by machining using wire Electrical Discharge Machining (EDM) and conventional machining, or by Metal Injection Molding (MIM), or it may be stamped at low cost from sheet material. Insulator 106 may be made by pressing and sintering, or by Ceramic Injection Molding (CIM).

Mechanical Coupling of the Electrode Assembly Components

Figure 14:
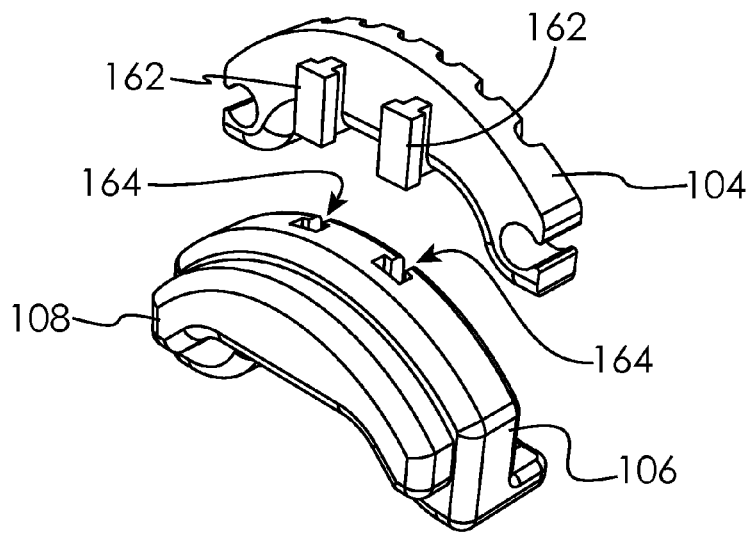
FIG. 14 is an exploded bottom perspective view of a ninth embodiment electrosurgical probe constructed in accordance with the principles of this invention.
Figure 15:
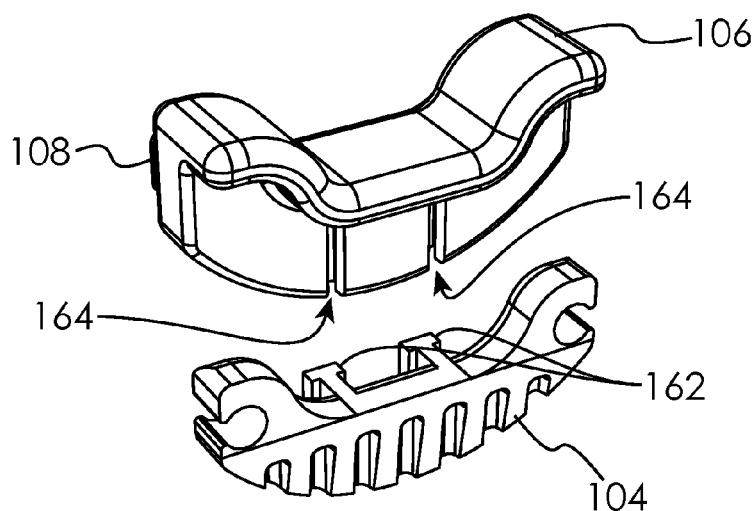
FIG. 15 is an exploded top perspective view of the ninth embodiment electrosurgical probe of FIG. 14.
Figure 16:
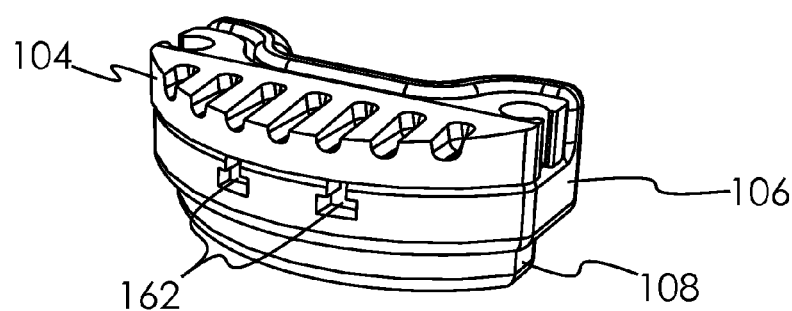
FIG. 16 is a bottom perspective view of the ninth embodiment electrosurgical probe of FIG. 14.

The various parts of the electrode assembly 102 may be mechanically coupled together. As shown in FIGS. 14-16, the active electrode 104 may have one or more first interlocking features 162 that mate with corresponding second interlocking features 164 formed into insulator 106. In the illustrated embodiment, first interlocking feature 162 comprises a male T-shaped protrusion that mates with a second interlocking feature 164 comprising a female T-shaped slot. Such an arrangement will prevent proximal movement of the active electrode 104 with respect to the insulator 106.

Figure 17:
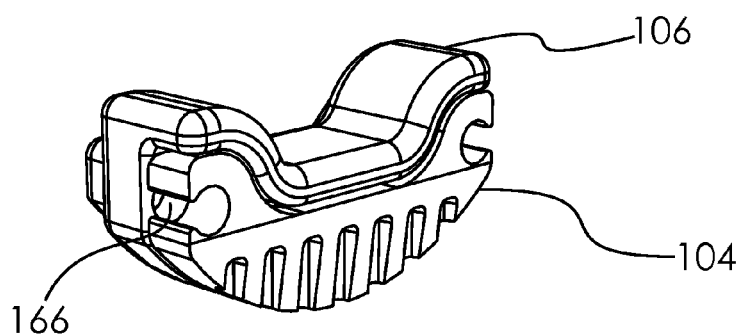
FIG. 17 is a perspective view of a tenth embodiment electrosurgical probe constructed in accordance with the principles of this invention.
Figure 18:
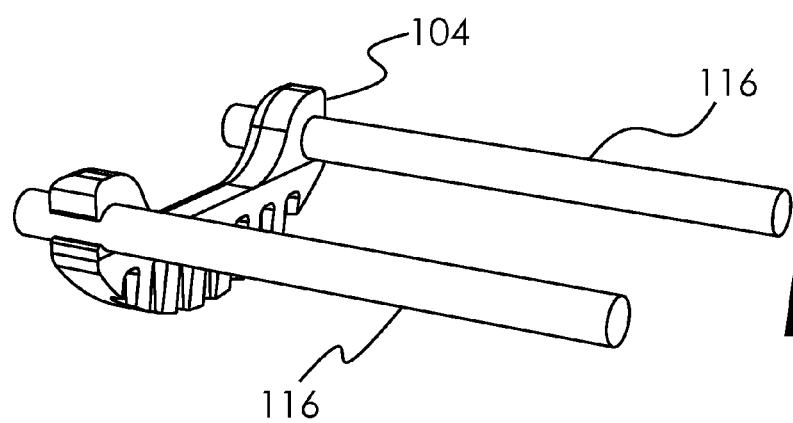
FIG. 18 is a perspective view of an active electrode and members of the tenth embodiment electro surgical probe of FIG. 17.
Figure 19:
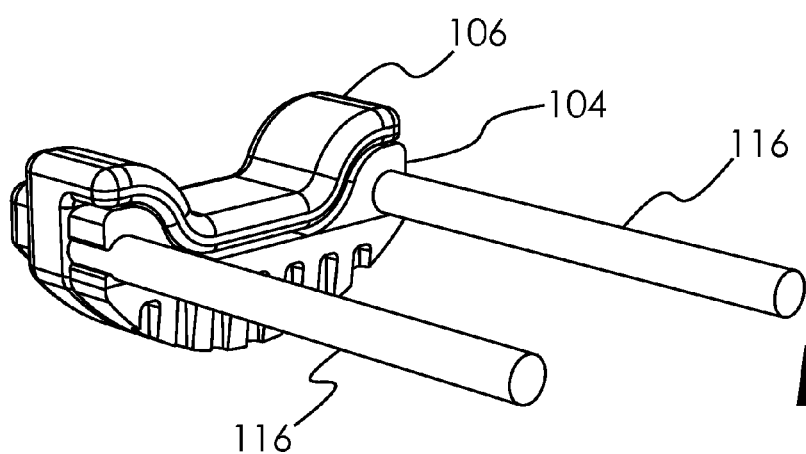
FIG. 19 is a perspective view of the tenth embodiment electro surgical probe of FIG. 17.

As shown in FIGS. 17-19, members 116 may be welded (or otherwise coupled) to the active electrode 104 such that the members 116 protrude distally from the active electrode 104. Insulator 106 may be formed with corresponding recesses 166 for receiving the distal portions of members 116. Such an arrangement prevents the active electrode 104 from moving downward (in the Z axis) relative to the insulator 106. Those skilled in the art will appreciate that use of the features of FIGS. 14-16 with the features of FIGS. 17-19 will constrain movement of the active electrode 104 with respect to the insulator 106 in both the Y and Z axes.

Figure 20:
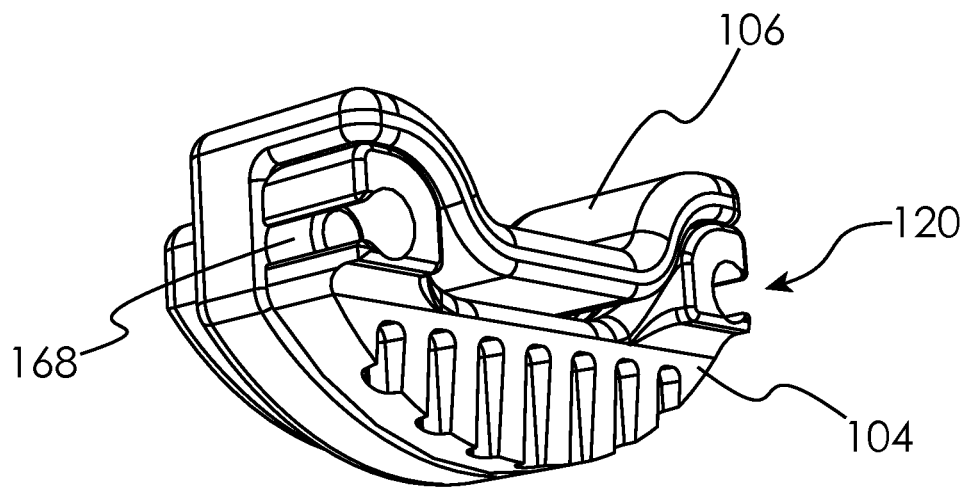
FIG. 20 is a perspective view of an eleventh embodiment electrosurgical probe constructed in accordance with the principles of this invention.
Figure 21:
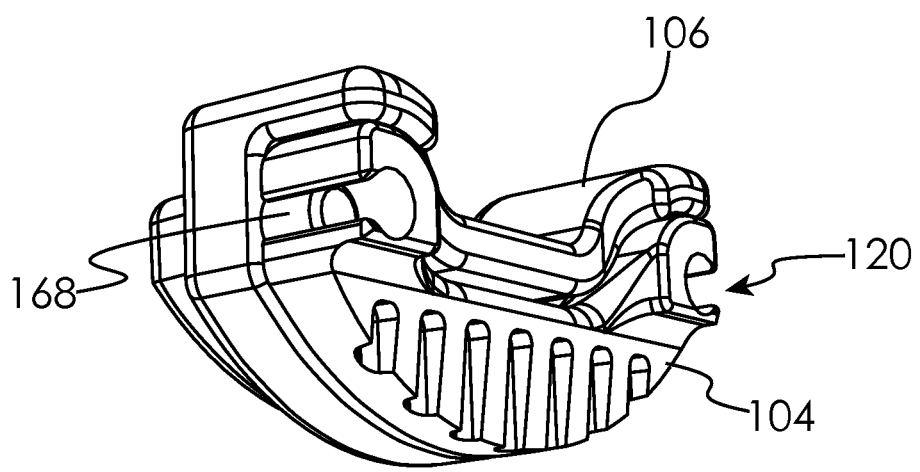
FIG. 21 is a perspective view of a twelfth embodiment electrosurgical probe constructed in accordance with the principles of this invention.
Figure 22:
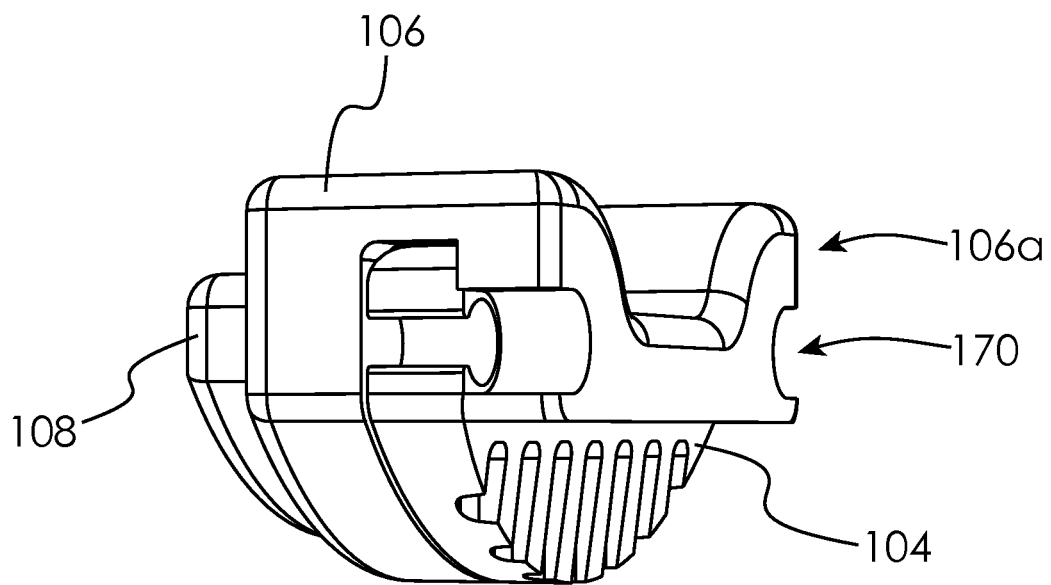
FIG. 22 is a perspective view of a thirteenth embodiment electrosurgical probe constructed in accordance with the principles of this invention.

As shown in FIGS. 20-21, the insulator 106 may include protrusions 168 that mate with the recesses 120 of active electrode 104. The protrusions 168 may fit snugly within the recesses 120 such that the active electrode is held securely to the insulator 106 by means of an interference fit. Alternatively, the active electrode 104 and the insulator 106 may be brazed, with the protrusions 168 providing alignment and support during the brazing process. In order to provide attachment points for the members 116, the area of active electrode 104 containing the recesses 120 may be extended in the proximal direction. In the embodiment shown in FIG. 20, the insulator 106 overhangs the proximal face of the active electrode 104 in order to cover the extended portions containing the recesses 120. In the embodiment of FIG. 21, the insulator 106 approximately follows the contours of the proximal face of the active electrode 104.

Figure 23:
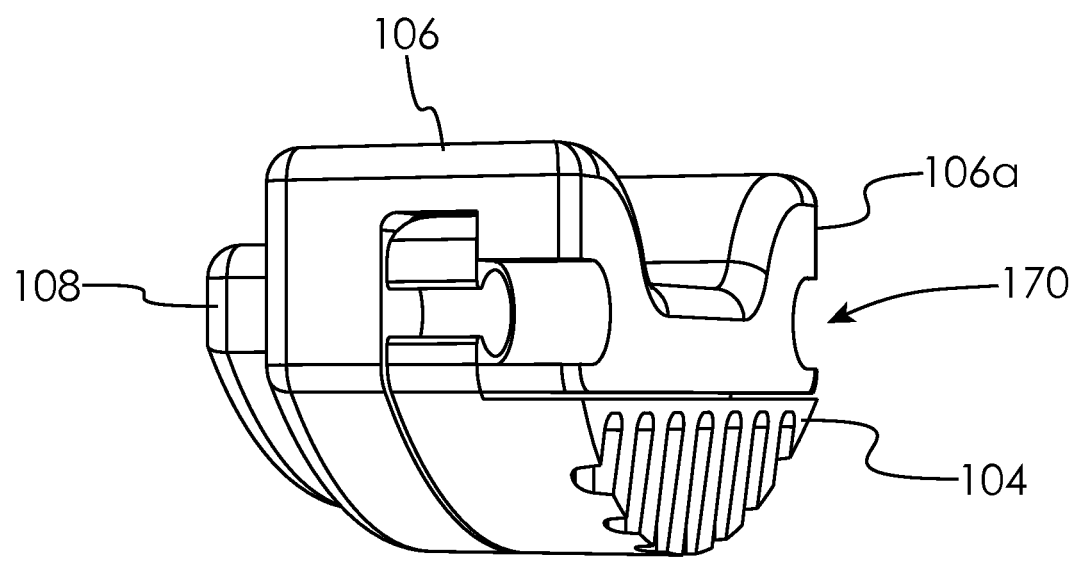
FIG. 23 is a perspective view of a fourteenth embodiment electrosurgical probe constructed in accordance with the principles of this invention.
Figure 24:
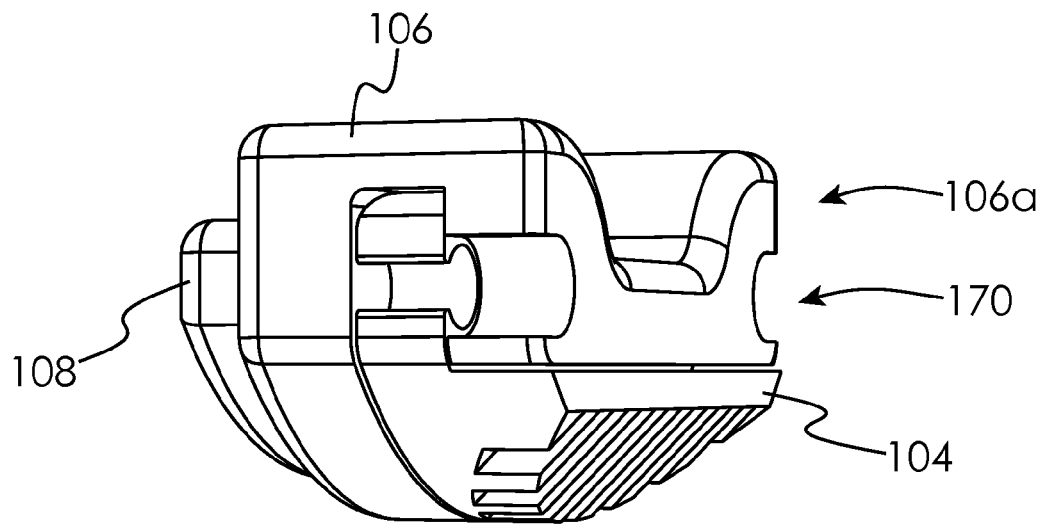
FIG. 24 is a perspective view of a fifteenth embodiment electrosurgical probe constructed in accordance with the principles of this invention.
Figure 25:
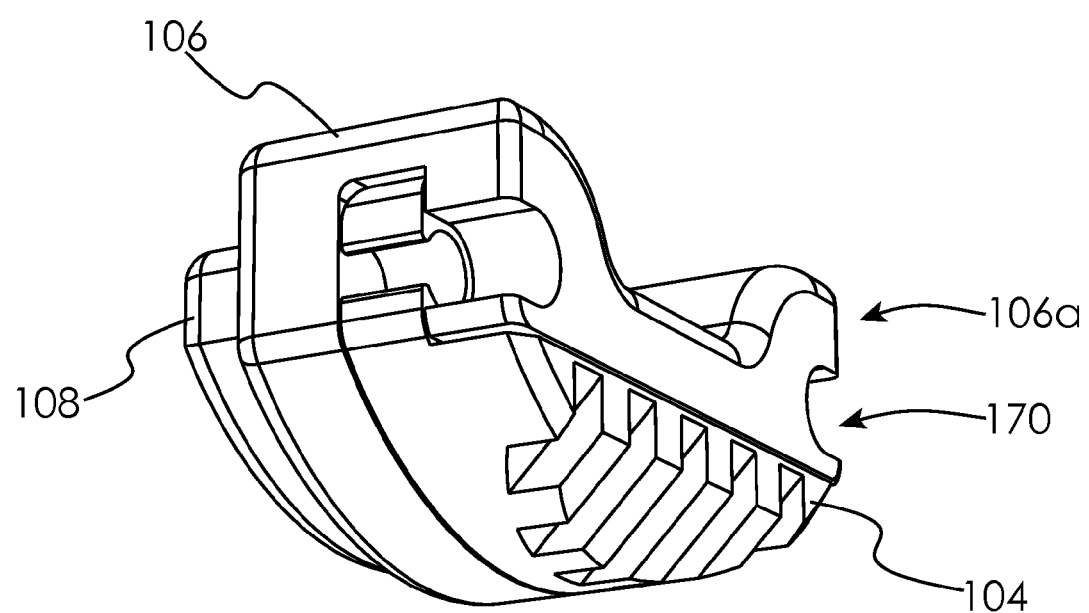
FIG. 25 is a perspective view of a sixteenth embodiment electrosurgical probe constructed in accordance with the principles of this invention.
Figure 26:
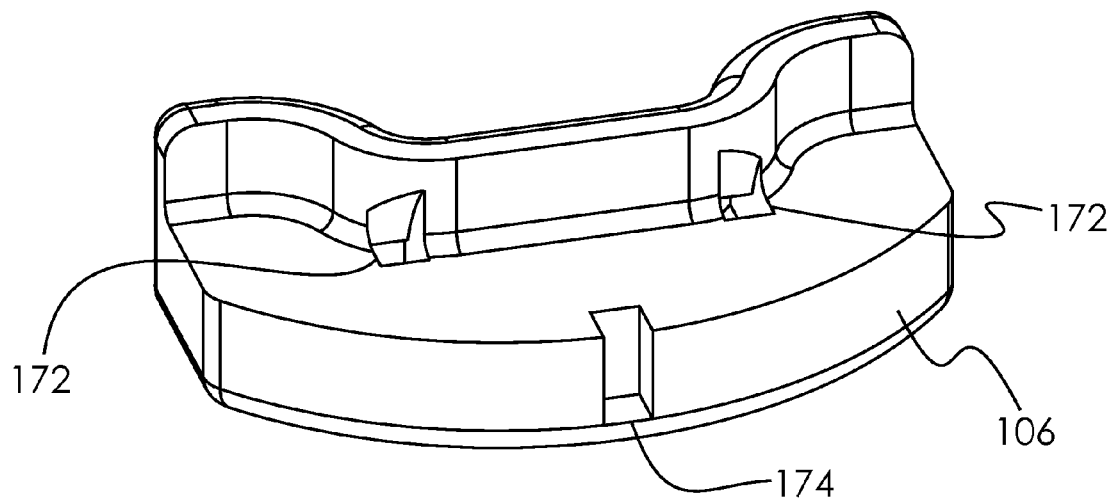
FIG. 26 is a perspective view of an insulator of a seventeenth embodiment electrosurgical probe constructed in accordance with the principles of this invention.
Figure 27:
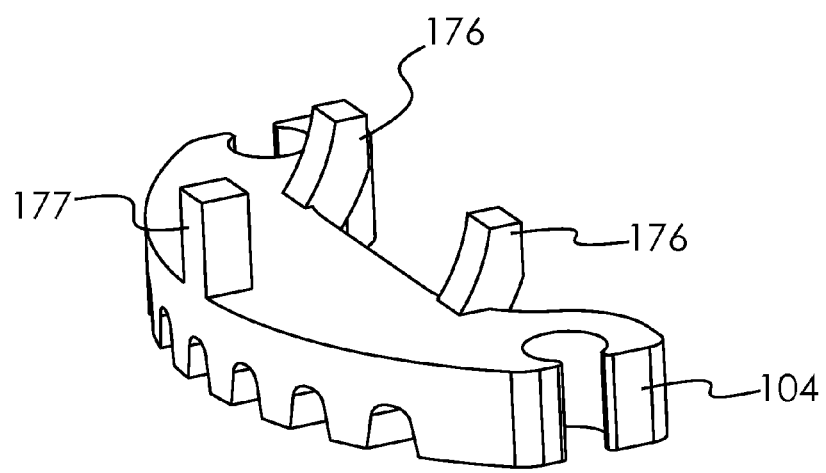
FIG. 27 is a perspective view of an active electrode of the seventeenth embodiment electrosurgical probe illustrated in FIG. 26.
Figure 28:
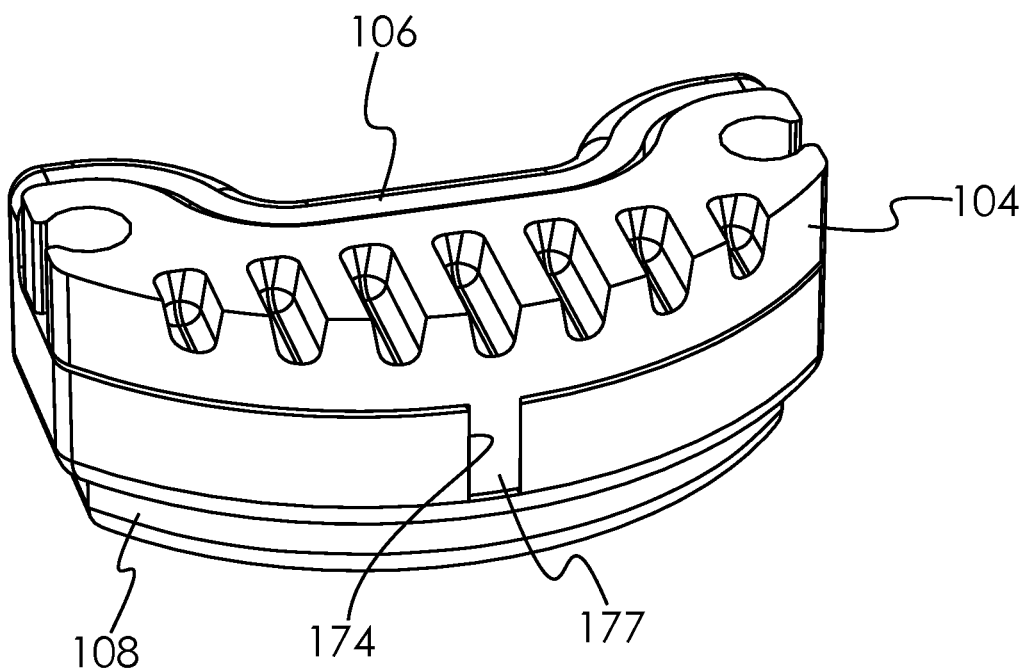
FIG. 28 is a perspective view of the seventeenth embodiment electrosurgical probe illustrated in FIG. 26.
Figure 29:
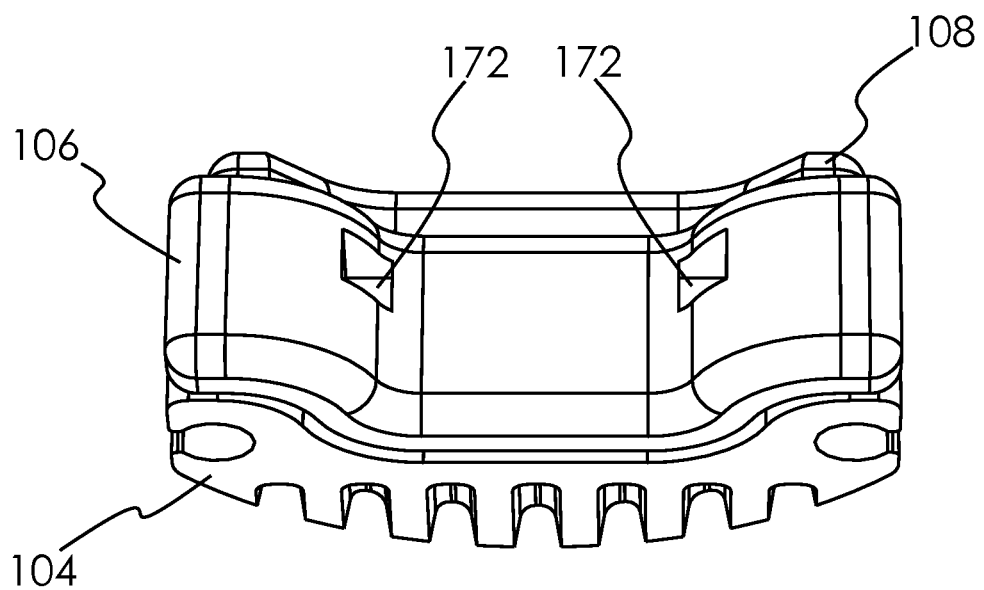
FIG. 29 is a perspective view of the seventeenth embodiment electrosurgical probe illustrated in FIG. 26.

As shown in FIGS. 22-25, the insulator 106 may include an overhang 106a that extends over a portion of the proximal side of the active electrode 104. The overhang 106a may include recesses 170 to allow for the passage of members 116. Such an arrangement prevents relative movement of the active electrode 104 with respect to the insulator 106 in any direction. In the embodiment of FIG. 23, the exposed portion of the proximal face of the active electrode is extended to be substantially flush with the proximal face of the insulator 106, making the active electrode 104 L-shaped in cross-section. As shown in the embodiments of FIGS. 24 and 25, the proximal face of active electrode 104 may be angled distally. In the embodiment of FIG. 24, the grooves 110 do not extend into the vertical portion of the proximal face of active electrode 104, but in the embodiment of FIG. 25, the grooves 110 do extend into the vertical portion of the proximal face of active electrode 104.

As shown in FIGS. 26-29, the insulator 106 may include female cavities 172 and 174 that receive corresponding male tabs 176 and 177 formed on the active electrode 104. Cavities 172 may be L-shaped such that tabs 176 may be bent once they are inserted into cavities 172, thereby retaining active electrode 104 in contact with the insulator 106. Once the tabs 176 are bent, the cavities 172 may optionally be backfilled with any desired insulating material, such as epoxy, to give just one non-limiting example.

Figure 30:
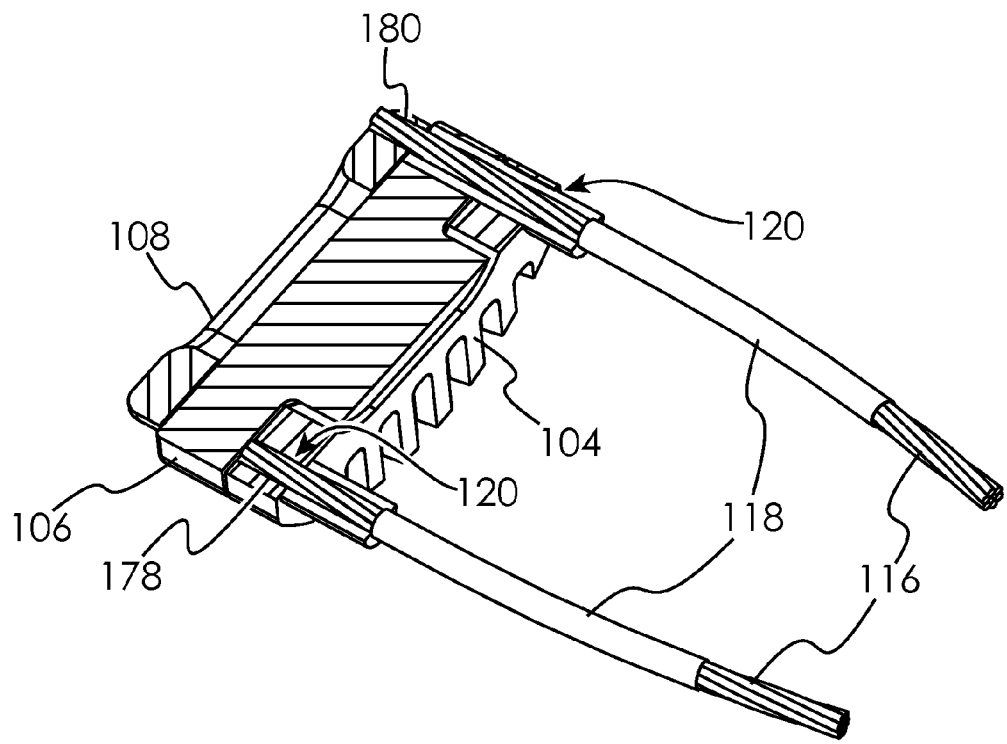
FIG. 30 is a top cross-sectional view of an eighteenth embodiment electrosurgical probe constructed in accordance with the principles of this invention.
Figure 31:
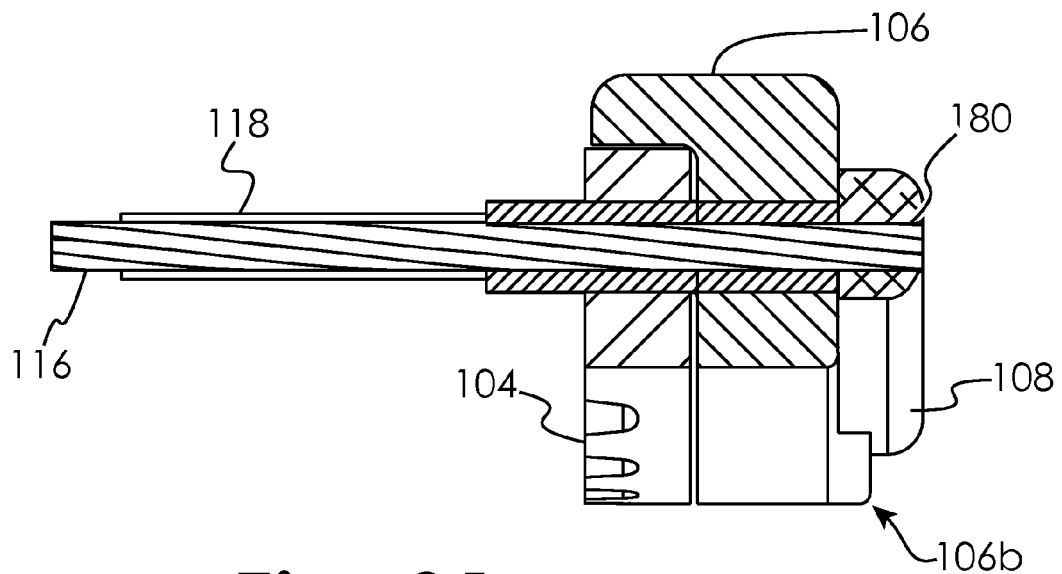
FIG. 31 is a side cross-sectional view of the eighteenth embodiment electrosurgical probe illustrated in FIG. 30.

FIG. 30 illustrates how the member 116 may be used to hold the assembly together. The powered wire 116 (lower wire in FIG. 30) is welded to the active electrode 104 at 178 within the passage 120. The unpowered member 116 (upper wire in FIG. 30) passes through the active electrode 104 and the insulator 106 and is welded to the floating electrode 108 at 180. The passage 120 through which the member 116/shield 118 passes through the active electrode 104 forms an interference fit with the shield 118 in some embodiments. Thus, the floating electrode 108 is held fast to the remainder of the assembly by means of the weld 180. As shown in FIG. 31, the insulator 106 may include an extension 106*b* to further support the floating electrode 108.

Braze Bonding the Components of the Electrode Assembly

Figure 34:
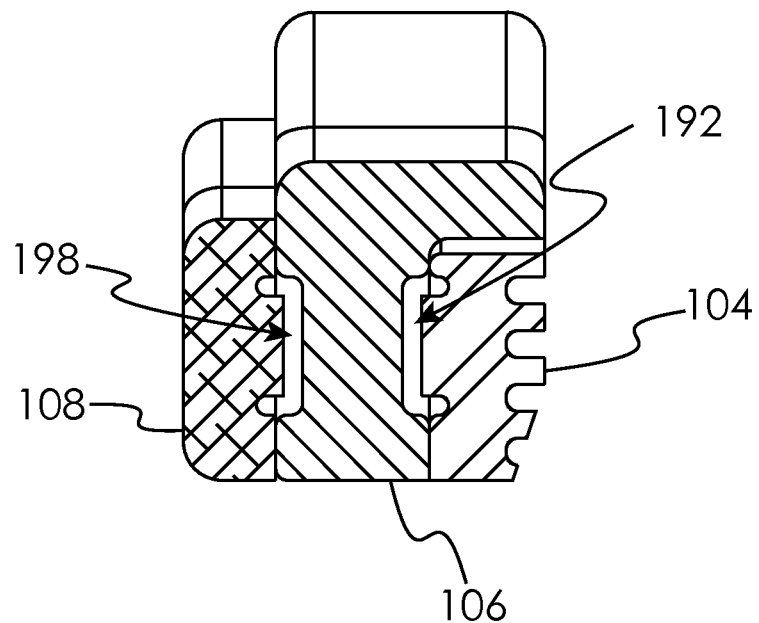
FIG. 34 is a side cross-sectional view of the nineteenth embodiment electrosurgical probe illustrated in FIGS. 32*a-c*.

In another embodiment, the components of electrode assembly 102 may be braze bonded together using high temperature ceramic-to-metal brazing (metallization brazing, active metal brazing, etc.). When using high temperature ceramic-to-metal brazing, the choice of materials for conductive and insulating components of the of electrode assembly 102 may take thermal expansion during brazing into account. In some embodiments, component surfaces may be planar, recessed, protruding and/or interlocked to facilitate parallelism and alignment of the various components. For example, FIGS. 32-34 illustrate various protrusions and recesses that facilitate the high temperature ceramic-to-metal brazing process. The rear surface of active electrode 104 may include protrusions 182 that fit within locator recesses 184 formed within the insulator 106 in order to facilitate alignment of these components during the high temperature ceramic-to-metal brazing operation. Similarly, the floating electrode 108 may include protrusions 186 that fit within locator recesses 188 formed within the insulator 106. The rear surface of active electrode 104 may also include a protrusion 190 that fits within a recess 192 formed within the insulator 106. The protrusion 190 may be formed, for example, during a Metal Injection Molding (MIM) process, and a recess 194 may be formed therearound to allow for braze overflow during the high temperature ceramic-to-metal brazing process. Similarly, the floating electrode 108 may also include a protrusion 196 that fits within a recess 198 formed within the insulator 106. The protrusion 196 may be formed, for example, during a Metal Injection Molding (MIM) process, and a recess 200 may be formed therearound to allow for braze overflow during the high temperature ceramic-to-metal brazing process. As can be seen in FIG. 34, in some embodiments the recesses 192 and 198 are formed larger than the respective protrusions 190 and 196 in order to allow room for the flow of metal during the high temperature ceramic-to-metal brazing process. Those skilled in the art will recognize that any illustrated protrusion and recess pair may be reversed and still achieve the same effect.

Figure 35:
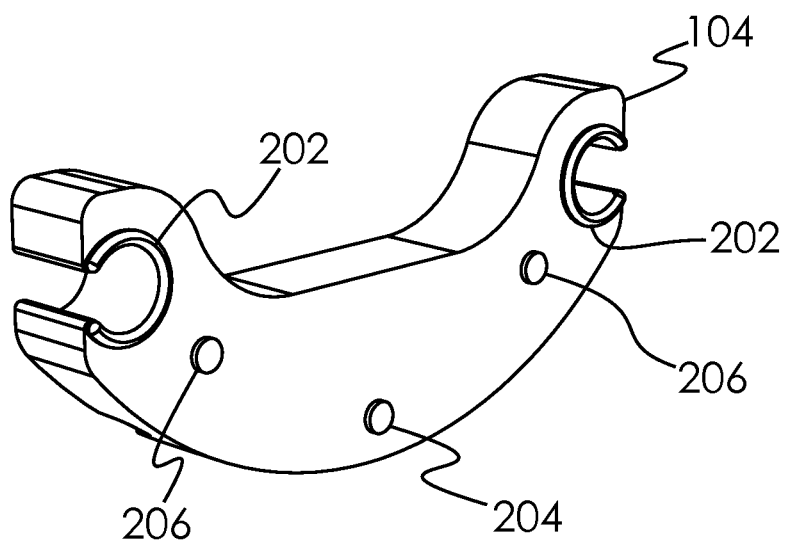
FIG. 35 is a perspective view of an active electrode of a twentieth embodiment electrosurgical probe constructed in accordance with the principles of this invention.

As shown in FIG. 35, the active electrode 104 may include rounded protrusions 202 around the recesses 120, as well as a protrusion 204 near the bottom of active electrode 104. The protrusions 202 and 204 create a defined gap between the active electrode 104 and the insulator 106 for placement of a disk (not shown) of brazing material. Such a gap prevents the active electrode 104 from possibly becoming misaligned with the insulator 106 during the brazing process. Additionally, provision of additional protrusions 206 in conjunction with the protrusion 204 will operate to increase the braze spot.

Other Means for Coupling of the Electrode Assembly Components

Alternatively, assembly 102 may be held together by other mechanical means, for example using fasteners such as screws, nuts, rivets or the like. The various parts of the electrode assembly 102 may also be adhesively coupled together.

Active electrode 104 may be joined to insulator 106, and insulator 106 may be joined to floating electrode 108 by a suitable biocompatible adhesive such as, for instance, EP42HT-2, EP62-1 MED or EP3HTMED epoxies by Master Bond Incorporated (Hackensack, N.J.) or Cement 31 by Sauereisen Incorporated (Pittsburgh, Pa.), all of which maintain their adhesive properties at the temperatures to which assembly 102 may be heated during use. Because members 116 conduct power to active electrode 104, it is not necessary to have a separate conductor to power the active electrode 104, thereby further reducing the cost of probe 100.

Attachment of Members 116

Figure 36:
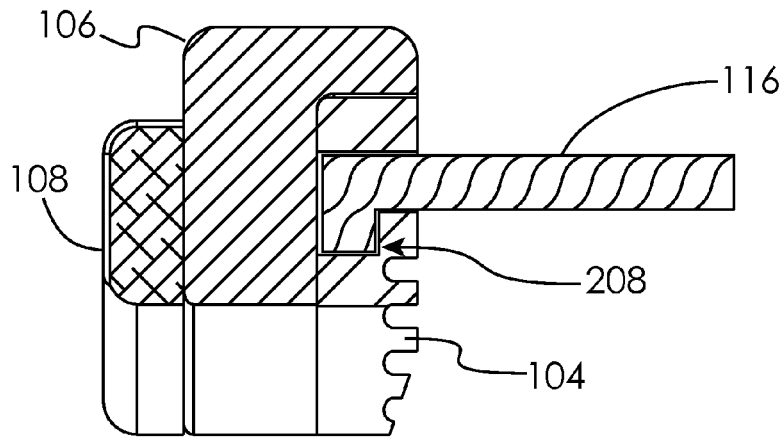
FIG. 36 is a cross-sectional view of a twenty-first embodiment electrosurgical probe constructed in accordance with the principles of this invention.
Figure 37:
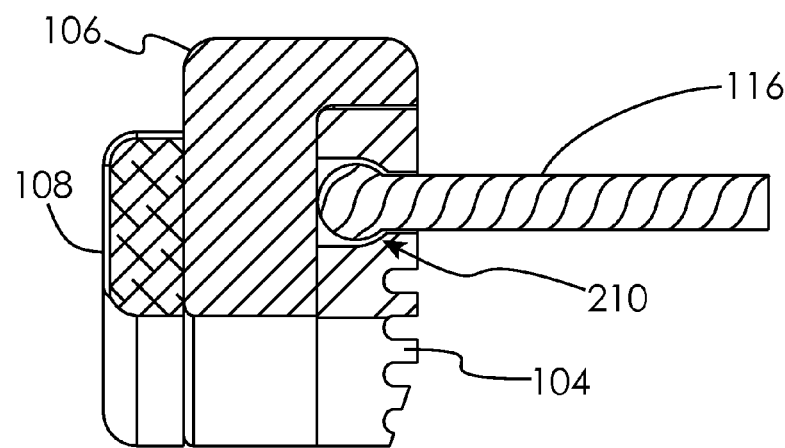
FIG. 37 is a cross-sectional view of a twenty-second embodiment electrosurgical probe constructed in accordance with the principles of this invention.
Figure 38:
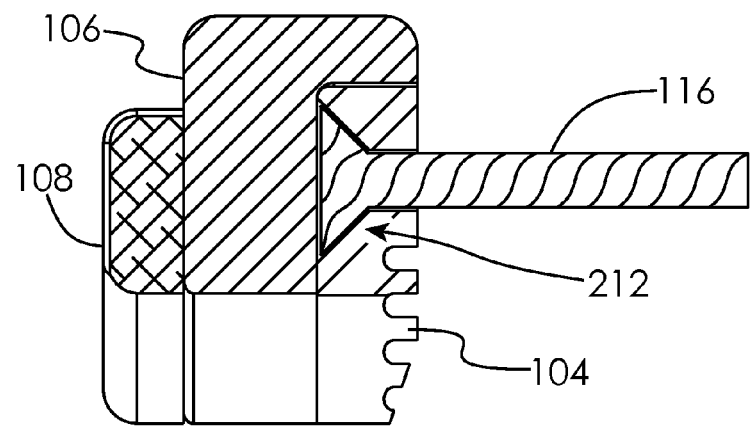
FIG. 38 is a cross-sectional view of a twenty-third embodiment electrosurgical probe constructed in accordance with the principles of this invention.

Members 116 may be attached to the active electrode 104 and/or the floating electrode 108 by means other than the welding process as discussed hereinabove. For example, the distal ends of the members 116 may be formed in a hooked configuration as shown in FIG. 36. The active electrode 104 may be formed with an appropriate recess 208 to accommodate the distal hook of the member 116. As an additional example, the distal ends of the members 116 may be formed in a spherical configuration as shown in FIG. 37. The active electrode 104 may be formed with an appropriate recess 210 to accommodate the distal sphere of the member 116. As an additional example, the distal ends of the members 116 may be formed in a flared configuration as shown in FIG. 38. The active electrode 104 may be formed with an appropriate recess 212 to accommodate the distal flare of the member 116. It will be appreciated by those skilled in the art that these distal end configurations of the members 116 prevent the members 116 from being moved proximally or distally relative to the active electrode 104 once assembled. Those skilled in the art will also recognize that any distal end formed on the member 116 that has an increased cross-sectional area will perform the same function of providing a mechanical interlock between the member 116 and the probe assembly 102.

Figure 39:
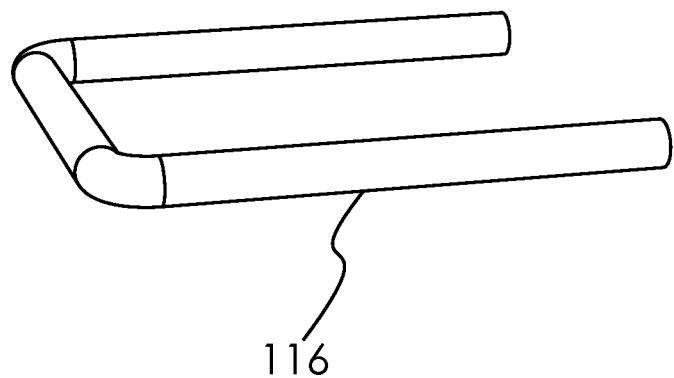
FIG. 39 is a perspective view of a member of a twenty-fourth embodiment electrosurgical probe constructed in accordance with the principles of this invention.
Figure 40:
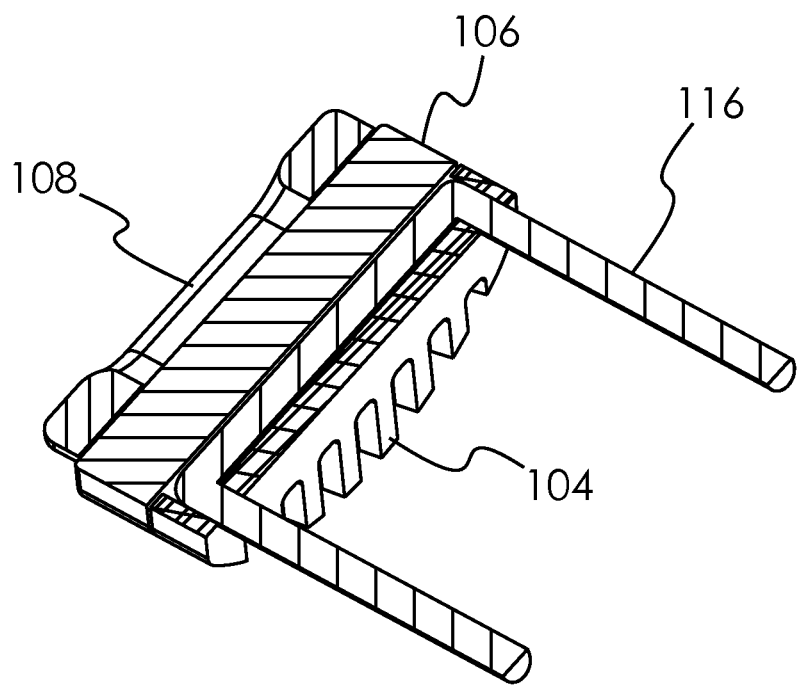
FIG. 40 is a cross-sectional view of the twenty-fourth embodiment electrosurgical probe illustrated in FIG. 39.

As shown in FIGS. 39-40, the members 116 may extend around the distal side of the active electrode 104 and be joined, thereby forming a loop that surrounds the active electrode 104. Since the member 116 is a single structure in this embodiment, either or both proximal ends of the member 116 may be connected to the power source that powers the active electrode 104.

Active Electrode Shields

Figure 41:
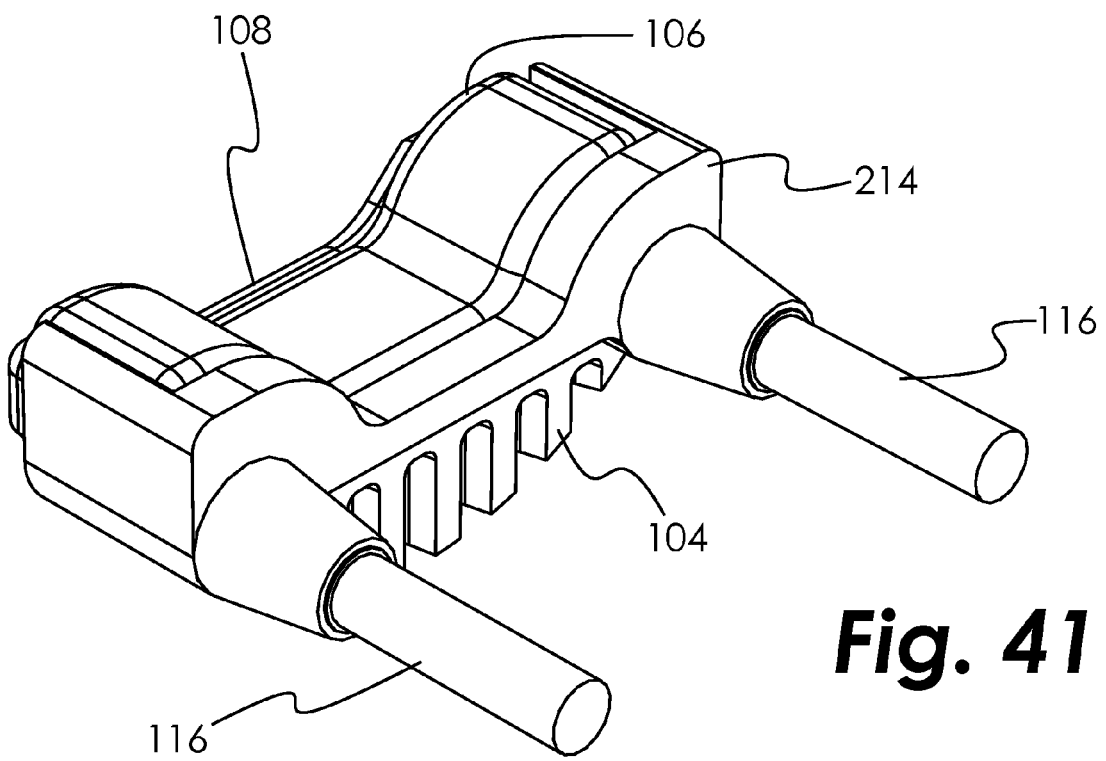
FIG. 41 is a perspective view of a twenty-fifth embodiment electrosurgical probe constructed in accordance with the principles of this invention.
Figure 42:
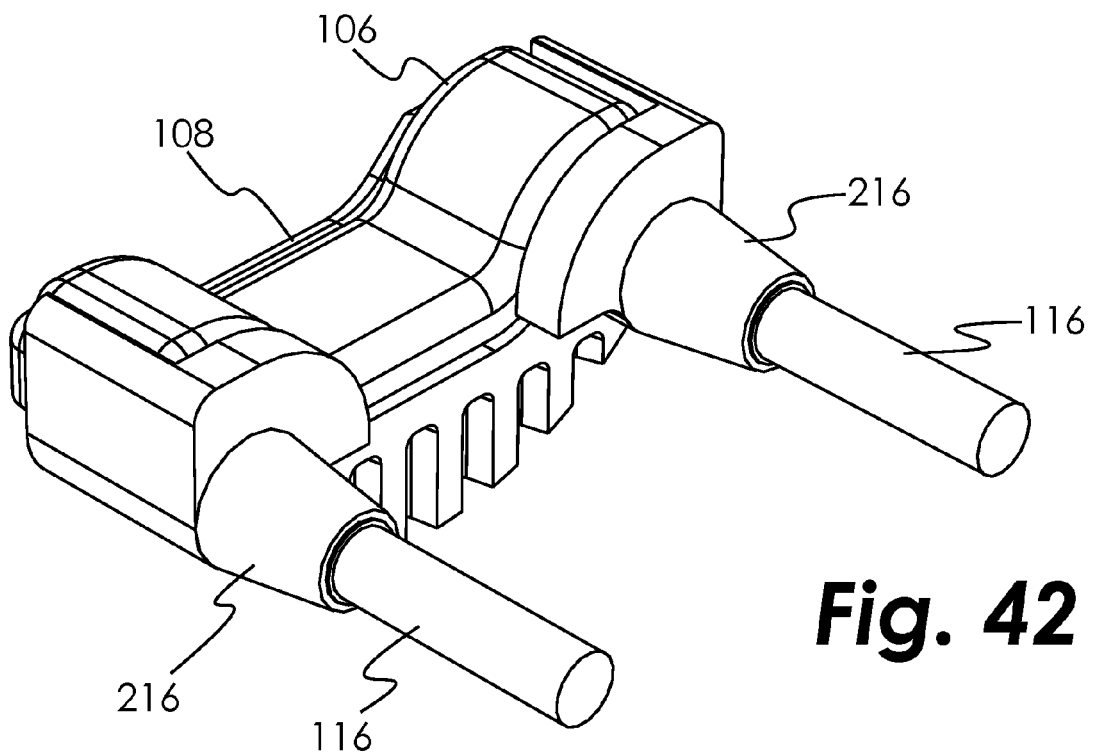
FIG. 42 is a perspective view of a twenty-sixth embodiment electrosurgical probe constructed in accordance with the principles of this invention.

Since power is supplied to the entire active electrode 104, it is desirable to shield portions of the active electrode 104 that are not intended to treat tissue. This is because current will be lost to surrounding tissue from these non-treatment sites of the active electrode 104, thereby reducing current density (and therefore effectiveness) in the treatment sites of the active electrode 104. As shown in FIG. 41, a shield 214 is placed across the proximal face of the active electrode 104 and extends distally along the sides thereof, in the regions not intended for treatment of tissue. With the use of shield 214, active electrode 104 surfaces which do not arc to tissue are shielded from power loss to surrounding tissue. Similar to shields 118, shield 214 therefore reduces current loss at exposed surfaces of the active electrode 104, thereby raising the device impedance and forcing the RF generator to supply more power to ignite the plasma when in partial or full contact with tissue at the treatment site. In an alternate embodiment illustrated in FIG. 42, the shielding is provided by two discrete shields 216. Shields 214 and 216 are preferably formed from a suitable dielectric material having a melting point high enough to prevent melting when the active electrode 104 is energized during use. Examples of suitable materials for insulator 106 and shields 118 include, but are not limited to, alumina, zirconia, and high-temperature polymers.

Figure 43:
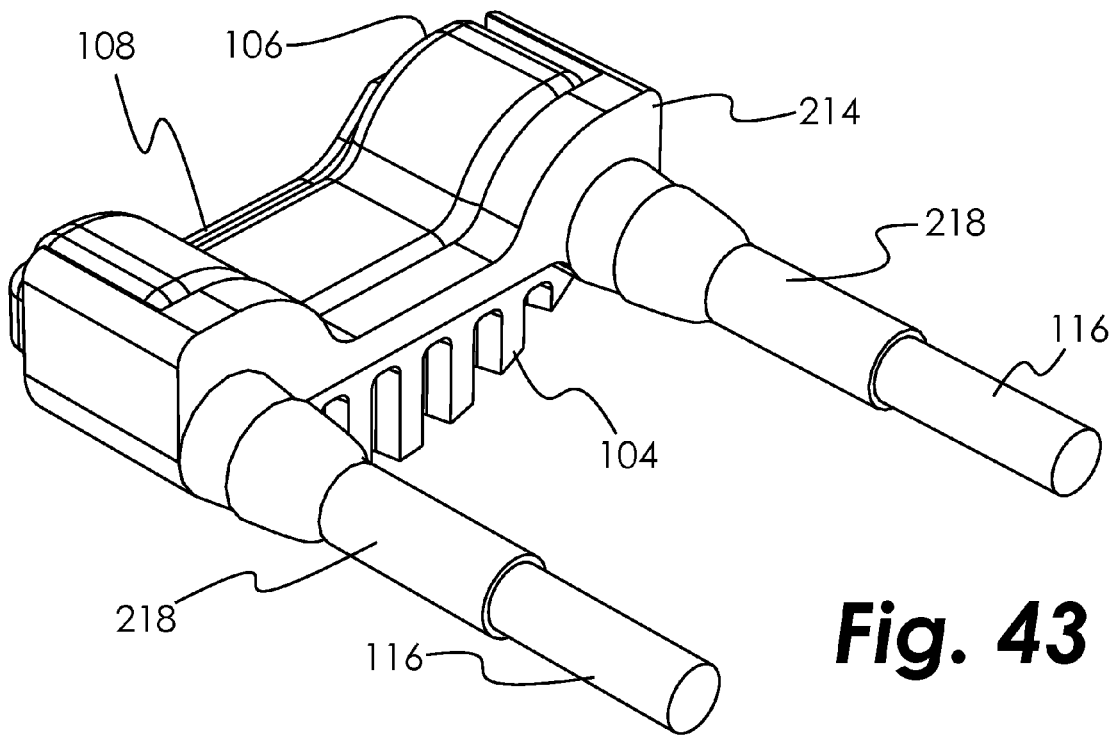
FIG. 43 is a perspective view of a twenty-seventh embodiment electrosurgical probe constructed in accordance with the principles of this invention.
Figure 44:
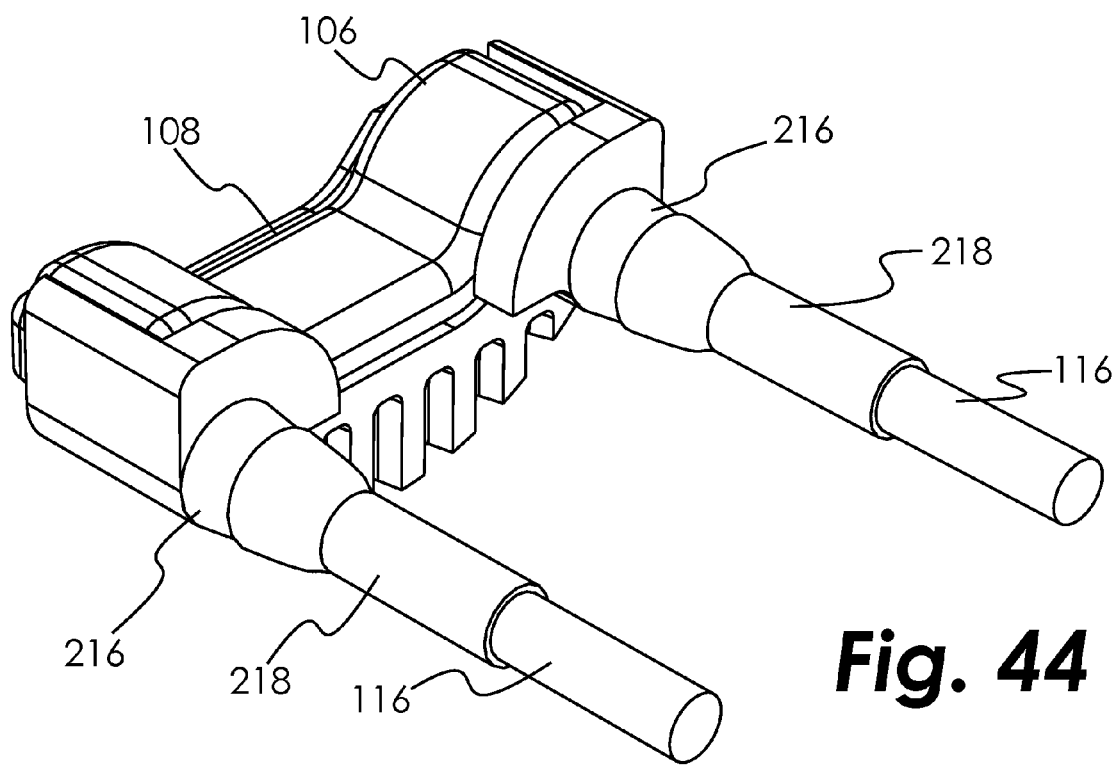
FIG. 44 is a perspective view of a twenty-eighth embodiment electrosurgical probe constructed in accordance with the principles of this invention.
Figure 45:
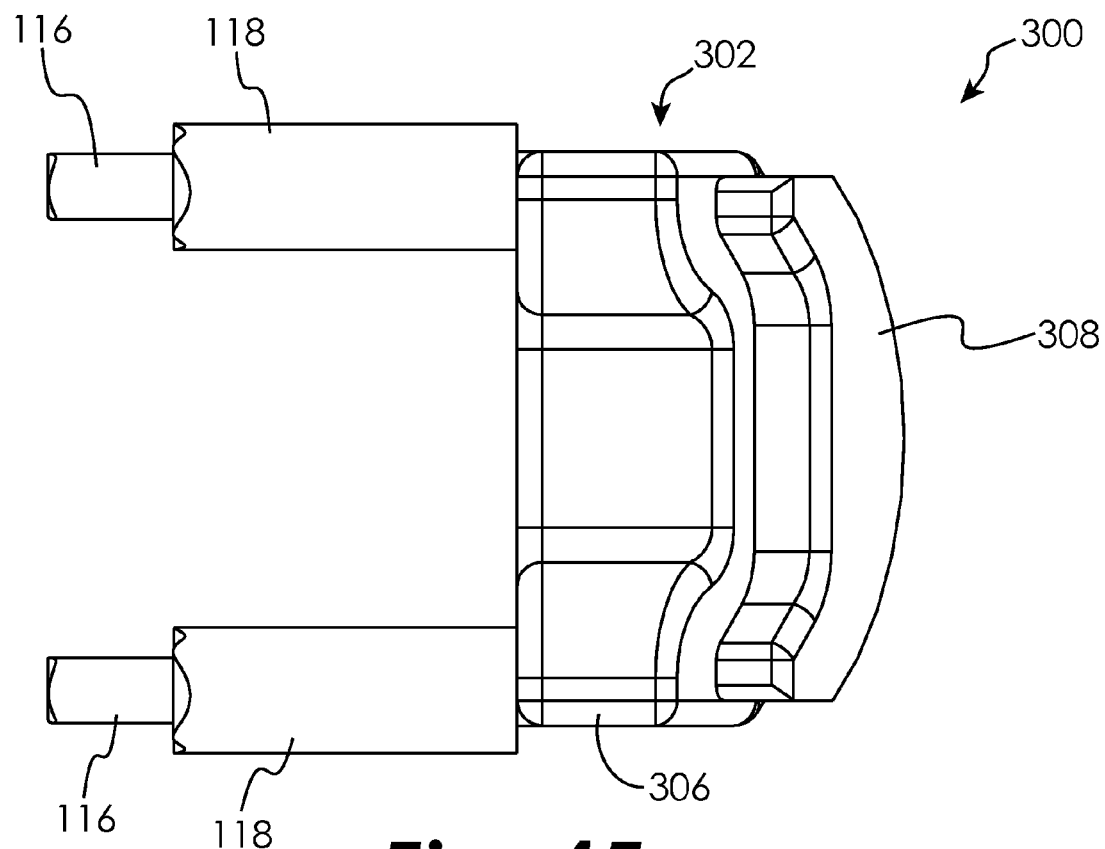
FIG. 45 is a top plan view of a twenty-seventh embodiment electrosurgical probe constructed in accordance with the principles of this invention.
Figure 46:
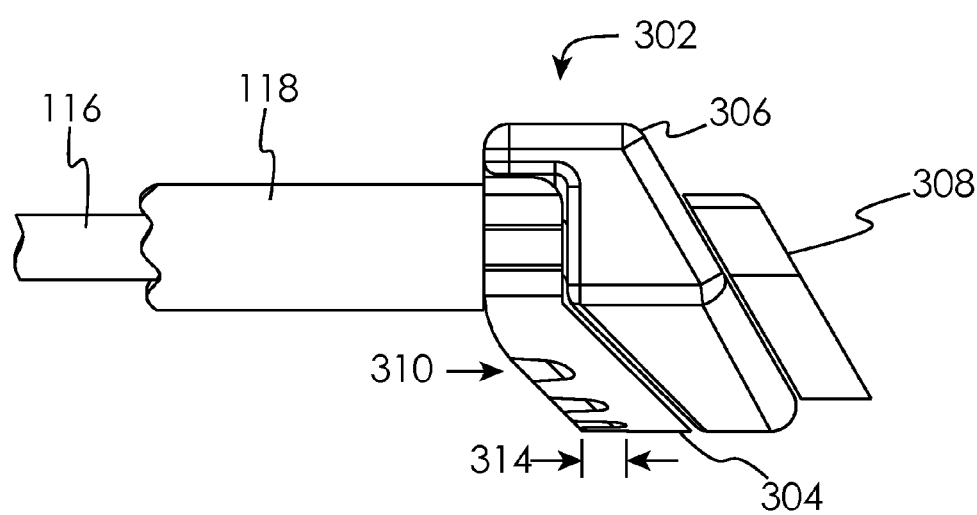
FIG. 46 is a side view of the electrosurgical probe of FIG. 45.
Figure 47:
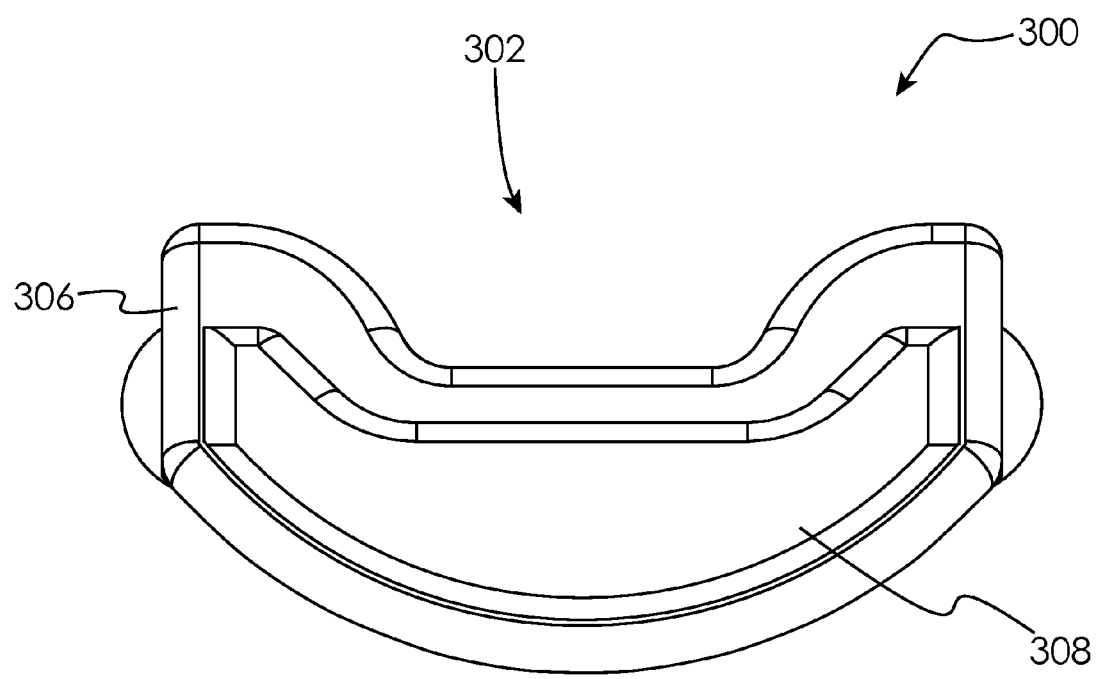
FIG. 47 is a distal end view of the electrosurgical probe of FIG. 45.

The shields 214 and 216 may be produced by any convenient method, such as machining or Ceramic Injection Molding (CIM), to give just two non-limiting examples. Each shield may extend proximally along the distal member 116 for robust insulation near the plasma zone. The shields 214 and 216 may be attached to the electrode assembly using any of the methods disclosed herein. Additionally, as illustrated in FIGS. 43 and 44, the shields 214 and 216 may be attached to the electrode assembly using high temperature resistant heat shrink tubing 218 extending over portions of the shields 214 and 216 and the members 116. When the heat shrink tubing 218 is exposed to a sufficiently high temperature, the tubing shrinks tightly around the portions of the shields 214 and 216 and the members 116, thereby holding them in joined relationship.

45 Degree Tip Configuration

Figure 48:
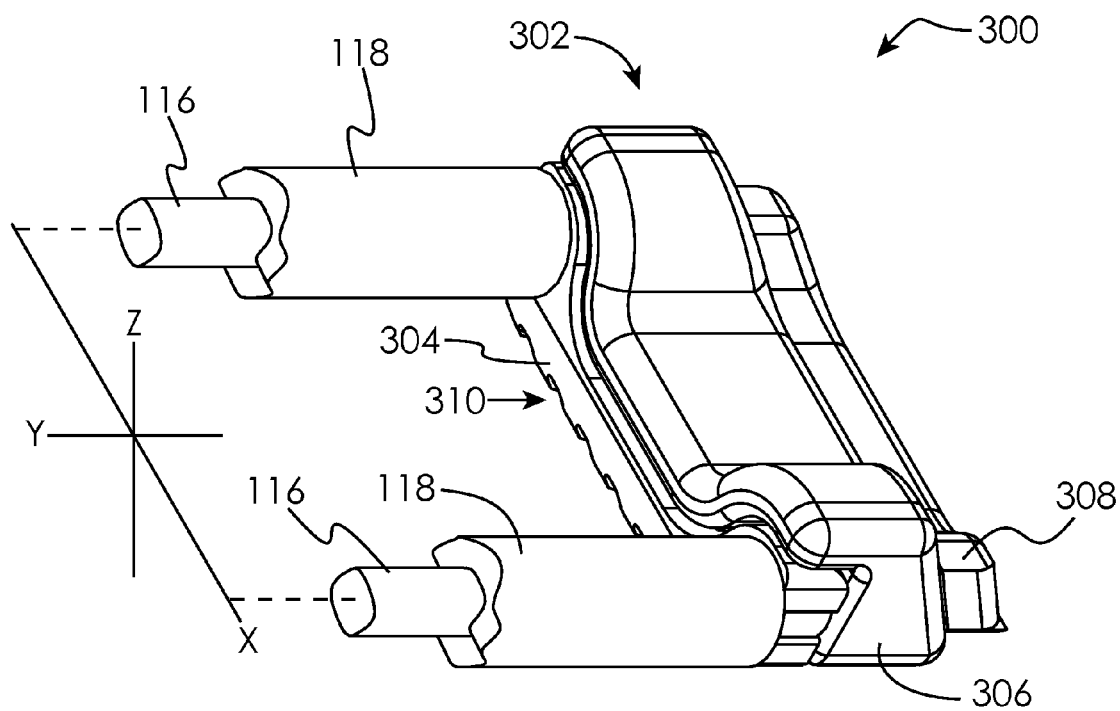
FIG. 48 is a perspective view of the electrosurgical probe of FIG. 45.
Figure 49:
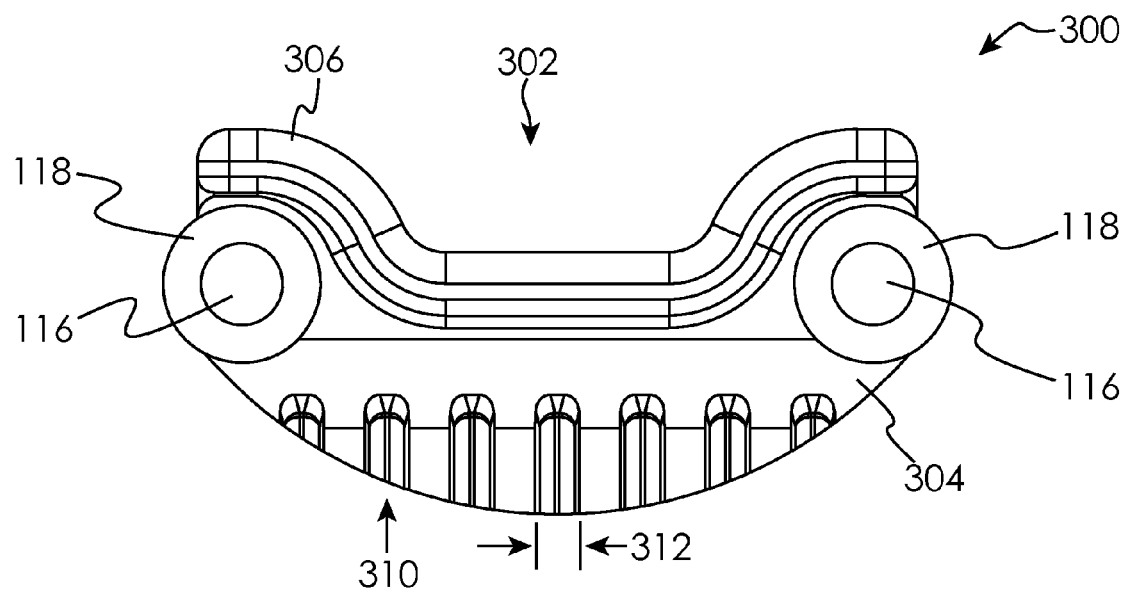
FIG. 49 is a proximal end view of the electrosurgical probe of FIG. 45.
Figure 50:
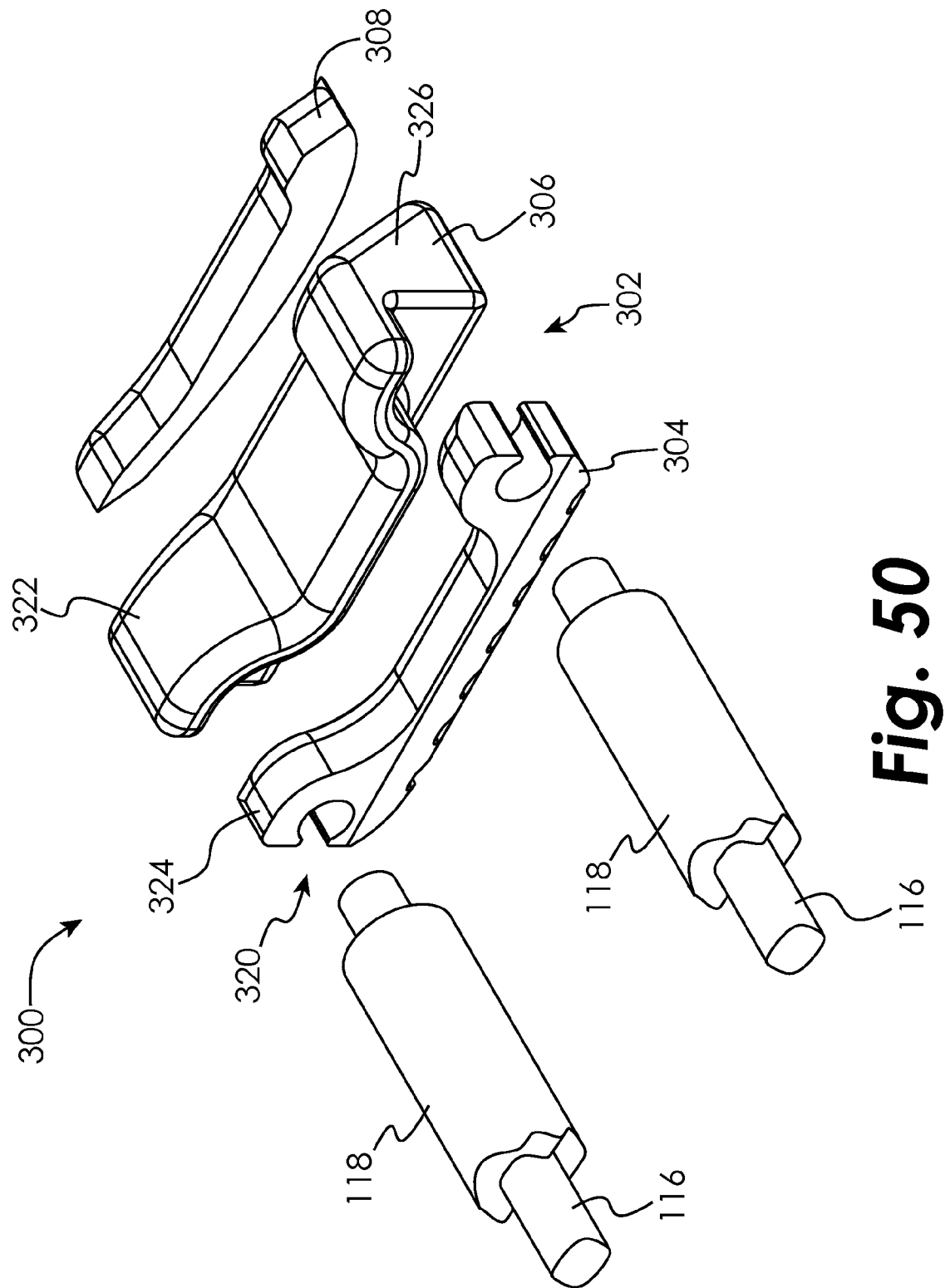
FIG. 50 is an exploded perspective view of the electrosurgical probe of FIG. 45.

In another embodiment, the electrosurgical probe tip is oriented at an approximate 45 degree angle to the longitudinal axis Y (see FIG. 48) of the resectoscope. Referring now to FIGS. 45-50, which depict the distal-most portion of probe 300, referred to herein as the active head, electrode assembly 302 includes active electrode 304, insulator 306 and floating electrode 308. Active electrode 304 has a plurality of grooves 310 of width 312 and depth 314, width 312 and depth 314 being selected to trap bubbles in the grooves. However, as noted previously, the present invention is not limited to the grooved design depicted but encompasses any active electrode ablating surface specifically configured to maximize bubble retention and concentrate power density. So long as the ablating surface performs the desired function (e.g., bubble retention, power density concentration), the specific design, geometry, arrangement and configuration of the array or its components is not particularly limited. Accordingly, the ablating surface may be composed of an array of raised and recessed regions, e.g., a plurality of walls and grooves, a plurality of elevated pins, a plurality of bumps and pockets, or a combination thereof. As noted previously, the array may be continuous or discontinuous, evenly or unevenly spaced, composed of raises and recesses that are linear or non-linear (e.g., curvilinear, wavy, zigzagged, angled, etc.), parallel or circumferential positioned, or the like. The grooves 310 increase the surface area in contact with the irrigating fluid to assist in bubble formation and also provide edges having high power density for electrical arcing to the surrounding tissue. The dimensions of the grooves are selected to trap bubbles in the grooves in order to increase the level of plasma formation. Active electrode 304 and floating electrode 308 may be formed from a suitable metallic material, examples of which include, but are not limited to, stainless steel, nickel, titanium, tungsten, molybdenum and the like. Insulator 306 may be formed from a suitable dielectric material, example of which include, but are not limited to, alumina, zirconia, and high-temperature polymers. Members 116, insulated by dielectric shields 118, are affixed to recesses 320 of active electrode 304 such that electrical power may be conducted by members 116 to active electrode 304. Members 116 are operably connected to a suitable RF generator for powering the active electrode 304. As best seen in FIG. 48, insulator 306 has a first portion 322 which insulates top surfaces 324 of active electrode 304, and a second portion 326 which electrically isolates floating electrode 308 from active electrode 304. When viewed axially in the distal direction as in FIG. 49, floating electrode 308 and second portion 326 of insulator 306 are flush with, or recessed behind active electrode 304.

Active electrode 304 incorporates a series of grooves 310 that facilitate entrapment of bubbles and plasma formation. With reference to FIG. 48, all points on the electrode assembly 302 are designed to be moved substantially in or parallel to the plane containing the axes X and Y, with the electrode assembly 302 reciprocating in directions coinciding with or parallel to the axis Y. The grooves 310 of the active electrode 304 have longitudinal axes that are oriented substantially 45 degrees from the plane containing the axes X and Z, and also oriented substantially 45 degrees from the plane containing the axes X and Y). Grooves 310 oriented in such a direction are referred to herein as vertical grooves for the sake of convenience. The present disclosure also contemplates horizontal grooves that are oriented substantially 90 degrees from the orientation of the vertical grooves, as well as grooves formed at angles intermediate thereto.

Variations in the configuration of the electrode assembly 302 and details of its manufacture, assembly and use are analogous to those described herein with respect to the 90 degree tip configuration.

Use of the Electrode Assembly

For the sake of brevity, the following discussion references probe 100. Those skilled in the art will appreciate that the discussion applies equally well to probe 300. Probe 100 is particularly useful for treating Benign Prostatic Hyperplasia (BPH), commonly referred to enlarged prostate. Surgical treatment of this condition is commonly accomplished using a resectoscope in a procedure referred to TransUrethral Resection of the Prostate (TURP). The resectoscope outer sheath is inserted into the urethra and the distal end advanced until it is near the prostate. The resectoscope working element with telescope and RF probe are inserted into the inner sheath such that the distal end of the probe can be used to modify or remove tissue. Most commonly, a cutting loop electrode (like that taught by Grossi et al in U.S. Pat. No. 4,917,082) is used to cut strips of tissue from the interior of the prostate, the site being filled with non-conductive irrigant. When sufficient tissue has been removed, the site including the bladder is flushed with irrigant to remove tissue strips that may remain at the site. The time required to flush the tissue from the site is frequently a significant portion of the total procedure time. Additionally, the use of non-conductive irrigant may lead to TUR syndrome, a potentially serious low blood sodium level. Gyrus ACMI (Southboro, Mass.) has developed bipolar RF devices which operate in conductive irrigant. One of the products removes tissue by bulk vaporization so as to make removal of remaining tissue strips after resection unnecessary. Because the system is bipolar, its efficiency is low. As a result, high power levels are required to achieve acceptably high tissue removal rates. As noted previously, excessive power levels can lead to unintended injury to local tissue. The bipolar products are usable with conductive irrigants only.

Probe 100 may be used to efficiently perform TURP procedures using either non-conductive or conductive irrigants. When non-conductive irrigant is introduced into the body, blood and other highly conductive bodily fluids contaminate the irrigant thereby making it conductive, the level of conductivity depending on the degree of contamination. When probe 100 is submerged in an irrigant with any level of conductivity, floating electrode 108 intensifies the electric field in close proximity to active electrode 104, thereby increasing the current density and making conditions more favorable for tissue vaporization. This allows probe 100 to be effectively used when either conductive or non-conductive irrigants are supplied to the site, the selection being based on surgeon preference.

Figure 51:
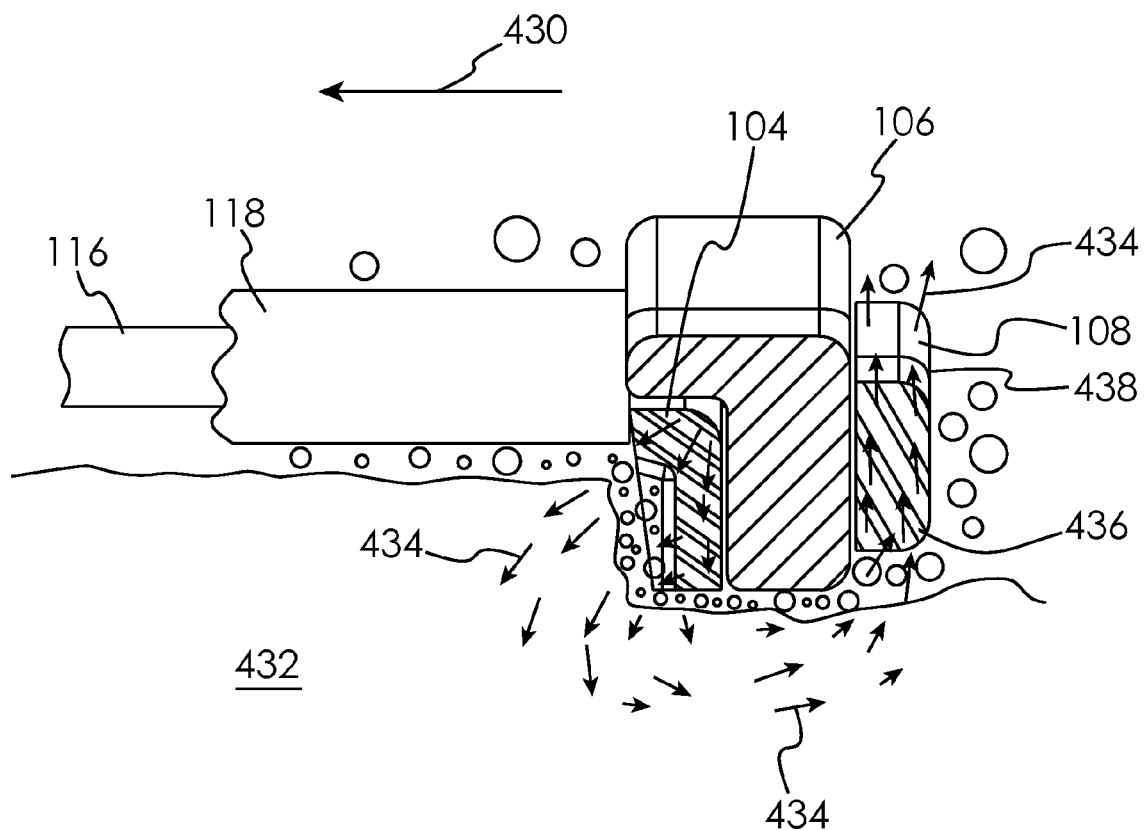
FIG. 51 is a cross-sectional view of the first embodiment electrosurgical probe illustrated in FIG. 1 in use on a tissue sample.

Referring to FIG. 51 depicting probe 100 in the context of a TURP procedure, probe 100 is moved in a proximal direction 430 relative to tissue 432. Current (indicated by arrows 434) from the RF generator, is supplied to active electrode 104 by one or more members 116. The current 434 then flows from active electrode 104 to a return electrode (not shown) and therefrom to the generator. A portion of the current flows through tissue 432 to tissue in close proximity to region 436 of floating electrode 108 in close proximity to active electrode 104. This current flows through floating electrode 108 to portion 438 of floating electrode 108 in a lower potential region of the electric field, and from floating electrode 108 to the irrigant and therethrough to the return electrode (not shown). Some of the current flowing from active electrode 104 to tissue 432 causes boiling of irrigant in close proximity, arcing within the bubbles formed, and vaporization of tissue in the manner previously herein described. A portion of the current flow at region 436 of floating electrode 108 may have sufficient density to cause boiling, arcing and vaporization of tissue. A larger portion of the current flow has insufficient density to causing boiling of the irrigant, but does cause heating of the irrigant to elevated temperatures less than 100° C. The heated irrigant in these regions of lower current density causes thermal modification of adjacent tissue, specifically dessication of the tissue resulting in hemo stasis.

When using probe 100 to perform a TURP, a resectoscope sheath is introduced to the site in the standard manner. The working element with telescope and probe 100 is inserted into the resectoscope sheath. Probe 100 is extended distally past the end of the prostate slightly into the bladder. The distal end of the resectoscope is lowered somewhat such that when probe 100 is energized and retracted proximally into the resectoscope, tissue intersected by active electrode assembly 102 is vaporized so as to form a channel or groove in the prostate tissue. The scope position is adjusted and the process repeated to remove additional tissue. The process is repeated until the required volume of tissue is removed. Current flowing between active electrode 104 and floating electrode 108 thermally coagulates adjacent tissue thereby producing hemostasis.

It will be appreciated by those skilled in the art that the presently disclosed embodiments can be used to vaporize tissue anywhere in the body where monopolar surgery in liquid can be tolerated. For example, the disclosed embodiments can be used for the removal of bladder tumors, to name just one non-limiting example.

While the disclosure has been illustrated and described in detail in the drawings and foregoing description, the same is to be considered as illustrative and not restrictive in character, it being understood that only certain embodiments have been shown and described and that all changes and modifications that come within the spirit of the disclosure are desired to be protected.

What is claimed:

1. An electrosurgical instrument connectable to an electrical power supply circuit, comprising:
    a conductive member having a member proximal end and a member distal end, the conductive member having a longitudinal axis;
    an active electrode coupled to said member distal end, said active electrode comprising: a proximal face, a bottom surface, and a top surface opposite said bottom surface, with said proximal face spanning between said bottom surface and said top surface;
        wherein said bottom surface of said active electrode is exposed for contact against patient tissue to be ablated; and
        at least one groove formed into said proximal face, said groove having a longitudinal axis extending in a direction from said bottom surface to said top surface;
    a floating electrode, said floating electrode being electrically isolated from said conductive member and constructed and arranged so that it is not electrically connected directly to the electrical power supply circuit when the electrosurgical instrument is connected to the electrical power supply circuit; and
    an insulator disposed between said active electrode and said floating electrode.

2. The electrosurgical instrument of claim 1, wherein said active electrode further comprises:
    at least one second groove formed into said proximal face, said at least one second groove oriented in a different direction than said at least one first groove and forming at least one intersection therewith.

3. The electrosurgical instrument of claim 1, wherein said proximal face is concave.

4. The electrosurgical instrument of claim 1, wherein said proximal face is convex.

5. The electrosurgical instrument of claim 1, said active electrode further comprising an opposite distal face, a first side joining said proximal face and said opposite distal face, and a second side opposite the first side and joining said proximal face and said opposite distal face; and
    wherein said insulator extends over at least a portion of said first and second sides.

6. The electrosurgical instrument of claim 1, wherein said active electrode further comprises at least one coupler of a first sex thereon;
    wherein said insulator further comprises at least one coupler of a second sex thereon; and
    wherein said at least one coupler of a first sex mates with respective ones of said at least one coupler of a second sex.

7. The instrument of claim 6, wherein:
    said at least one coupler of a first sex comprises at least one male T-shaped protrusion; and
    said at least one coupler of a second sex comprises at least one female T-shaped slot.

8. The instrument of claim 6, wherein:
    said at least one coupler of a first sex comprises at least one tab; and
    said at least one coupler of a second sex comprises at least one cavity.

9. The electrosurgical instrument of claim 1,
    wherein said active electrode further comprises at least one first hole formed therein;
    wherein said insulator comprises at least one second hole formed therein; and
    wherein said member distal end extends through said at least one first hole and into said at least one second hole.

10. The electrosurgical instrument of claim 1,
    wherein said active electrode further comprises at least one first hole formed therein;

wherein said insulator comprises at least one first protrusion formed thereon; and wherein said at least one first protrusion extends into a respective one of said at least one first hole.

11. The instrument of claim 10, wherein said member distal end extends into said at least one first hole.

12. The electrosurgical instrument of claim 1, wherein said active electrode comprises an opposite distal face opposite said proximal face, a first side joining said proximal face and said opposite distal face, and a second side opposite said first side and joining said proximal face and said opposite distal face; and wherein said insulator extends over at least a first portion of said proximal face.

13. The instrument of claim 12, wherein:

said first portion of said proximal face lies in a first plane; and a second portion of said proximal face lies in a second plane.

14. The instrument of claim 13, wherein said first and second planes are parallel.

15. The electrosurgical instrument of claim 1, wherein a first cross-sectional area of said member distal end is larger than a second cross-sectional area of said member proximal end;

said active electrode has an active electrode distal face, said active electrode further having a passage formed therethrough, wherein said passage comprises a recess at said active electrode distal face, said passage having a larger cross-sectional area at said active electrode distal face than at said active electrode proximal face; and wherein said conductive member is disposed in said passage such that said member distal end is positioned within said recess.

16. An electrosurgical instrument connectable to an electrical power supply circuit, comprising:

a first conductive member having a first member proximal end and a first member distal end;

a second member having a second member proximal end and a second member distal end;

an active electrode coupled to said first member distal end, wherein the active electrode has a proximal face, a bottom surface, and a top surface opposite said bottom surface, with said proximal face spanning between said bottom surface and said top surface, wherein said bottom surface is exposed for contact against patient tissue to be ablated, and wherein a plurality of grooves are formed into said proximal face having longitudinal axes extending in a direction from said bottom surface to said top surface;

a floating electrode coupled to said second member distal end;

an insulator disposed between said active electrode and said floating electrode;

wherein said floating electrode is electrically isolated from said active electrode and is constructed and arranged so that it is not electrically connected directly to the electrical power supply circuit when the electrosurgical instrument is connected to the electrical power supply circuit; and wherein said second member is electrically isolated from said active electrode.

17. The instrument of claim 16, wherein said first member distal end is welded to said active electrode.

18. An electrosurgical instrument connectable to an electrical power supply circuit, comprising:

a member having a first member proximal end and a second member proximal end, said first and second member proximal ends being joined at a member distal end thereby forming a loop;

an active electrode having an active electrode proximal face, an active electrode distal face, an active electrode bottom surface exposed for contact against patient tissue to be ablated, and an active electrode top surface opposite said active electrode bottom surface, said proximal face having a plurality of grooves formed therein, said grooves extending from a bottom edge of said proximal face bounding said bottom surface to a position intermediate said bottom edge of said proximal face and a top edge of said proximal face bounding said top surface, and said active electrode further having a first passage formed therethrough and a second passage formed therethrough, said member passing through said first and second passages;

a floating electrode, said floating electrode being electrically isolated from said member and constructed and arranged so that it is not electrically connected directly to the electrical power supply circuit when the electrosurgical instrument is connected to the electrical power supply circuit; and an insulator disposed between said active electrode and said floating electrode.

19. An electrosurgical instrument connectable to an electrical power supply circuit, comprising:

a conductive member having a member proximal end and a member distal end;

an active electrode coupled to said member distal end, said active electrode having a substantially flat proximal face, a bottom surface, a top surface opposite said bottom surface, with said proximal face spanning between said bottom surface and said top surface, and a plurality of grooves formed into said proximal face, said grooves extending from a bottom edge of said proximal face bounding said bottom surface to a position intermediate said bottom edge of said proximal face and a top edge of said proximal face bounding said top surface;

a floating electrode, said floating electrode being electrically isolated from said conductive member and constructed and arranged so that it is not electrically connected directly to the electrical power supply circuit when the electrosurgical instrument is connected to the electrical power supply circuit;

an insulator disposed between said active electrode and said floating electrode; and a dielectric shield disposed over a first portion of said active electrode, said dielectric shield having a melting point high enough to prevent the dielectric shield from melting when the active electrode is energized.

20. The electrosurgical instrument of claim 19, wherein said dielectric shield is additionally disposed over a second portion of said conductive member.

* * * * *